US012207963B2

United States Patent
Liu et al.

(10) Patent No.: US 12,207,963 B2
(45) Date of Patent: *Jan. 28, 2025

(54) IMAGE GENERATION BY HIGH DENSITY ELEMENT SUPPRESSION

(71) Applicant: Hologic, Inc., Marlborough, MA (US)

(72) Inventors: Xiaomin Liu, Sunnyvale, CA (US); Haili Chui, Fremont, CA (US); Xiangwei Zhang, Fremont, CA (US); Nikolaos Gkanatsios, Newtown, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/509,550

(22) Filed: Nov. 15, 2023

(65) Prior Publication Data

US 2024/0260923 A1    Aug. 8, 2024

Related U.S. Application Data

(63) Continuation of application No. 17/280,866, filed as application No. PCT/US2019/052621 on Sep. 24, 2019, now Pat. No. 11,857,358.

(Continued)

(51) Int. Cl.
*G06K 9/00*    (2022.01)
*A61B 6/00*    (2006.01)
(Continued)

(52) U.S. Cl.
CPC ............ *A61B 6/5258* (2013.01); *A61B 6/461* (2013.01); *A61B 6/502* (2013.01); *G06T 11/008* (2013.01);
(Continued)

(58) Field of Classification Search
CPC ....... A61B 6/5258; A61B 6/461; A61B 6/502; A61B 6/5235; A61B 6/5241;
(Continued)

(56) References Cited

U.S. PATENT DOCUMENTS 3,502,878 A    3/1970  Stewart
3,863,073 A    1/1975  Wagner
(Continued)

FOREIGN PATENT DOCUMENTS

CN    108135580          6/2018
CN    108135580  A  *   6/2018  ........... A61B 8/0825
(Continued)

OTHER PUBLICATIONS

PCT International Search Report and Written Opinion in International Application PCT/US2019/052621, mailed Dec. 13, 2019, 10 pages.
(Continued)

*Primary Examiner* — Xin Jia
(74) *Attorney, Agent, or Firm* — Merchant & Gould P.C.

(57) ABSTRACT

A method and breast imaging system for processing breast tissue image data includes feeding image data of breast images to an image processor, identifying image portions depicting breast tissue and high density elements and executing different processing methods on input images. A first image processing method involves breast tissue enhancement and high density element suppression, whereas the second image processing method involves enhancing high density elements. Respective three-dimensional sets of image slices may be generated by respective image processing methods, and respective two-dimensional synthesized images are generated and combined to form a two-dimensional composite synthesized image which is presented through a display of the breast imaging system. First and
(Continued)

second image processing may be executed on generated three-dimensional image sets or two-dimensional projection images acquired by an image acquisition component at respective angles relative to the patient's breast.

20 Claims, 20 Drawing Sheets

Related U.S. Application Data

(60) Provisional application No. 62/738,244, filed on Sep. 28, 2018.

(51) Int. Cl.
  *A61B 6/46* (2024.01)
  *A61B 6/50* (2024.01)
  *G06T 11/00* (2006.01)

(52) U.S. Cl.
  CPC ............... *G06T 2207/10116* (2013.01); *G06T 2207/30068* (2013.01)

(58) Field of Classification Search
  CPC ............... A61B 5/4312; A61B 8/0825; A61B 2090/3908; A61B 2090/3966; A61B 2576/02; A61B 6/025; G06T 11/008; G06T 2207/10116; G06T 2207/30068; G06T 2207/10016; G06T 5/003; G06T 5/50; G06T 7/0012; G16H 30/40
  See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels et al. |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch et al. |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,359,637 A | 10/1994 | Webber |
| 5,365,562 A | 11/1994 | Toker |
| 5,404,152 A | 4/1995 | Nagai |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,501,819 B2 | 12/2002 | Unger et al. |
| 6,515,685 B1 | 2/2003 | Halverson |
| 6,525,713 B1 | 2/2003 | Soeta et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,751,780 B1 | 6/2004 | Neff et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,025,725 B2 | 4/2006 | Dione et al. |
| 7,110,490 B2 | 9/2006 | Eberhard |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,606,801 B2 | 10/2009 | Faitelson et al. |
| 7,630,533 B2 | 12/2009 | Ruth et al. |
| 7,702,142 B2 | 4/2010 | Ren et al. |
| 7,760,924 B2 | 7/2010 | Ruth et al. |
| 7,840,905 B1 | 11/2010 | Weber |
| 8,239,784 B2 | 8/2012 | Hotelling |
| 8,571,289 B2 | 10/2013 | Ruth et al. |

(56) References Cited

U.S. PATENT DOCUMENTS

| | | |
|---|---|---|
| 8,712,127 B2 | 4/2014 | Ren et al. |
| 8,799,013 B2 | 8/2014 | Gustafson |
| 8,842,806 B2 | 9/2014 | Packard |
| 9,084,579 B2 | 7/2015 | Ren |
| 9,795,357 B2 | 10/2017 | Carelsen |
| 9,811,758 B2 | 11/2017 | Ren |
| 9,962,138 B2 | 5/2018 | Schweizer |
| 10,076,295 B2 | 9/2018 | Gemmel |
| 10,111,631 B2 | 10/2018 | Gkanatsios et al. |
| 10,206,644 B2 | 2/2019 | Kim |
| 10,248,882 B2 | 4/2019 | Ren |
| 10,679,095 B2 | 6/2020 | Ren |
| 10,922,897 B2 | 2/2021 | Maeda |
| 11,650,672 B2 | 5/2023 | Mellett |
| 11,857,358 B2 | 1/2024 | Liu |
| 2001/0038681 A1 | 11/2001 | Stanton et al. |
| 2001/0038861 A1 | 11/2001 | Hsu et al. |
| 2002/0012450 A1 | 1/2002 | Tsujii |
| 2002/0050986 A1 | 5/2002 | Inoue et al. |
| 2002/0075997 A1 | 6/2002 | Unger et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0149364 A1 | 8/2003 | Kapur |
| 2003/0194050 A1 | 10/2003 | Eberhard et al. |
| 2003/0194051 A1 | 10/2003 | Wang et al. |
| 2003/0194115 A1 | 10/2003 | Kaufhold et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0001094 A1 | 1/2004 | Unnewehr |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0140656 A1 | 6/2005 | McLoone |
| 2005/0226375 A1 | 10/2005 | Eberhard et al. |
| 2006/0026535 A1 | 2/2006 | Hotelling |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0021877 A1 | 1/2008 | Saito |
| 2008/0045833 A1 | 2/2008 | Defreitas et al. |
| 2008/0109740 A1 | 5/2008 | Prinsen et al. |
| 2008/0130979 A1 | 6/2008 | Ren et al. |
| 2008/0187095 A1* | 8/2008 | Boone ............... A61B 8/0825 378/37 |
| 2008/0262874 A1 | 10/2008 | Toshimutsu |
| 2008/0267467 A1 | 10/2008 | Sokulin et al. |
| 2009/0003519 A1 | 1/2009 | Defreitas et al. |
| 2009/0010384 A1 | 1/2009 | Jing et al. |
| 2009/0033522 A1 | 2/2009 | Skillman |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0174663 A1 | 7/2009 | Rudd |
| 2009/0213034 A1 | 8/2009 | Wu et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0083154 A1 | 4/2010 | Takeshita |
| 2010/0086188 A1 | 4/2010 | Ruth et al. |
| 2010/0135558 A1 | 6/2010 | Ruth et al. |
| 2010/0194682 A1 | 8/2010 | Orr |
| 2010/0195882 A1 | 8/2010 | Ren et al. |
| 2010/0226475 A1 | 9/2010 | Smith et al. |
| 2010/0325088 A1 | 12/2010 | Hsieh et al. |
| 2011/0137132 A1 | 6/2011 | Gustafson |
| 2011/0270358 A1 | 11/2011 | Davis |
| 2011/0282686 A1 | 11/2011 | Venon |
| 2011/0314405 A1 | 12/2011 | Turner |
| 2012/0131498 A1 | 5/2012 | Gross et al. |
| 2012/0133600 A1 | 5/2012 | Marshall et al. |
| 2012/0154431 A1 | 6/2012 | Fram |
| 2012/0275656 A1 | 11/2012 | Boese et al. |
| 2013/0239063 A1 | 9/2013 | Ubillos |
| 2013/0259193 A1 | 10/2013 | Packard |
| 2014/0013280 A1 | 1/2014 | Yoshioka et al. |
| 2014/0033126 A1* | 1/2014 | Kreeger ............... G06T 11/003 715/833 |
| 2014/0123183 A1 | 5/2014 | Fujimoto |
| 2014/0140604 A1 | 5/2014 | Carton et al. |
| 2014/0143710 A1 | 5/2014 | Zhao |
| 2014/0282216 A1 | 9/2014 | Baker |
| 2014/0314205 A1 | 10/2014 | Carelsen |
| 2015/0094581 A1 | 4/2015 | Butler |
| 2015/0260816 A1 | 9/2015 | Liang |
| 2015/0309712 A1 | 10/2015 | Marshall et al. |
| 2015/0317434 A1 | 11/2015 | Kondo |
| 2015/0374325 A1 | 12/2015 | Shimizu |
| 2016/0162163 A1 | 6/2016 | Park et al. |
| 2016/0166222 A1 | 6/2016 | Kim |
| 2016/0235386 A1 | 8/2016 | Schweizer |
| 2016/0296185 A1 | 10/2016 | Gemmel |
| 2016/0364122 A1 | 12/2016 | Shimomura |
| 2016/0367120 A1 | 12/2016 | Dupont et al. |
| 2017/0038914 A1 | 2/2017 | Kawagishi |
| 2017/0065238 A1 | 3/2017 | Smith et al. |
| 2018/0137385 A1 | 5/2018 | Ren |
| 2018/0211421 A1* | 7/2018 | Wicklein ............. A61B 6/5258 |
| 2019/0196662 A1 | 6/2019 | Mitchell |
| 2019/0221046 A1 | 7/2019 | Maeda |
| 2019/0325255 A1 | 10/2019 | Ren |
| 2020/0363877 A1 | 11/2020 | Mellett |
| 2020/0373013 A1 | 11/2020 | Cao |
| 2022/0015731 A1 | 1/2022 | Liu |
| 2022/0020475 A1 | 1/2022 | Chen et al. |
| 2022/0172824 A1 | 6/2022 | Solis |
| 2023/0107616 A1 | 4/2023 | Saba |

FOREIGN PATENT DOCUMENTS

| | | |
|---|---|---|
| EP | 775467 | 5/1997 |
| EP | 982001 | 3/2000 |
| EP | 1004957 | 5/2000 |
| EP | 1428473 | 6/2004 |
| EP | 2783632 | 10/2014 |
| EP | 2913769 | 9/2015 |
| EP | 2952376 | 12/2015 |
| JP | 2000-322198 | 11/2000 |
| JP | 2004-038947 | 2/2004 |
| JP | 2004-357789 | 12/2004 |
| JP | 2007029260 A | 2/2007 |
| JP | 2007-282656 | 11/2007 |
| JP | 2007-330374 | 12/2007 |
| JP | 2008-503253 | 2/2008 |
| JP | 2008-073436 | 4/2008 |
| JP | 2008-199293 | 8/2008 |

(56) References Cited

FOREIGN PATENT DOCUMENTS

| | | | |
|---|---|---|---|
| JP | 2010-086149 | 4/2010 | |
| JP | 2011/044295 | 4/2011 | |
| JP | 2014-068874 | 4/2014 | |
| JP | 2014-104099 | 6/2014 | |
| JP | 2017-000664 | 1/2017 | |
| WO | 1990/05485 | 5/1990 | |
| WO | 1998/16903 | 4/1998 | |
| WO | 00/51484 | 9/2000 | |
| WO | 03/020114 | 3/2003 | |
| WO | 2005/051197 | 6/2005 | |
| WO | 2005/110230 | 11/2005 | |
| WO | 2005/112767 | 12/2005 | |
| WO | 2006/055830 | 5/2006 | |
| WO | 2006/058160 | 6/2006 | |
| WO | WO-2011044295 A2 * | 4/2011 | ............. A61B 6/025 |
| WO | 2011/066486 | 6/2011 | |
| WO | 2012/071429 | 5/2012 | |
| WO | 2014/183183 | 11/2014 | |
| WO | 2018/183548 | 10/2018 | |
| WO | 2018/183549 | 10/2018 | |
| WO | 2018/183550 | 10/2018 | |
| WO | WO-2019032558 A1 * | 2/2019 | ............. G06T 5/008 |

OTHER PUBLICATIONS

PCT International Preliminary Report on Patentability in International Application PCT/US2019/052621, mailed Apr. 8, 2021, 8 pages.

"Layer Basics—Adobe Press", published Apr. 6, 2017; https://www.adobepress.com/articles/article.asp?p=2756476&seqNum=4.

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98/5493, Nov. 1998.

Dobbins JT et al. "Digital x-ray tomosynthesis: current state of the art and clinical potential" Physics in Medicine and Biology vol. 48, No. 19, pp. 65-81 (2003).

Essentials for life: Senographe Essential Full-Field Digital Mammography System, GE Health-care Brochure, MM-0132-05.06-ENUS, 2006.

Filtered Back Projection, (NYGREN) published May 8, 2007; URL: http://web.archive.org/web/1999101013 I 715/http://www.owlnet.rice.edu/-elec539/Projects97/cult/node2.html.

Grant, DG, "Tomosynthesis, a three dimensional imagine technique", IEEE Trans. Biomed Engineering, vol. BME-19, #1, Jan. 1972, pp. 20-28.

Heang-Ping Chan et al., "ROC study of the effect of stereoscopic imaging on assessment of breast lesions", Medical Physics, vol. 32, No. 4, Apr. 2005.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Lorad Selenia Document B-BI-SEO US/Intl (May 2006) copyright Hologic 2006.

Mammographic Accreditation Phantom, http://www.cirsinc.com/pdfs/015cp.pdf.

Pediconi, Federica et al., "Color-coded automated signal intensity curve for detection and characterization of breast lesions: Preliminary evaluation of a new software for MR-based breast imaging", International Congress Series 1281 (2005) 1081-1086.

Senographe 700 & 800T (GE); 2-page download on Jun. 22, 2006 from www.gehealthcare.com/inen/rad/whe/products/mswh800t.html.; Figures 1-7 on 4 sheets relateral shift compression paddle.

Smith, A., "Fundamentals of Breast Tomosynthesis", White Paper, Hologic Inc., WP-00007, Jun. 2008.

\* cited by examiner

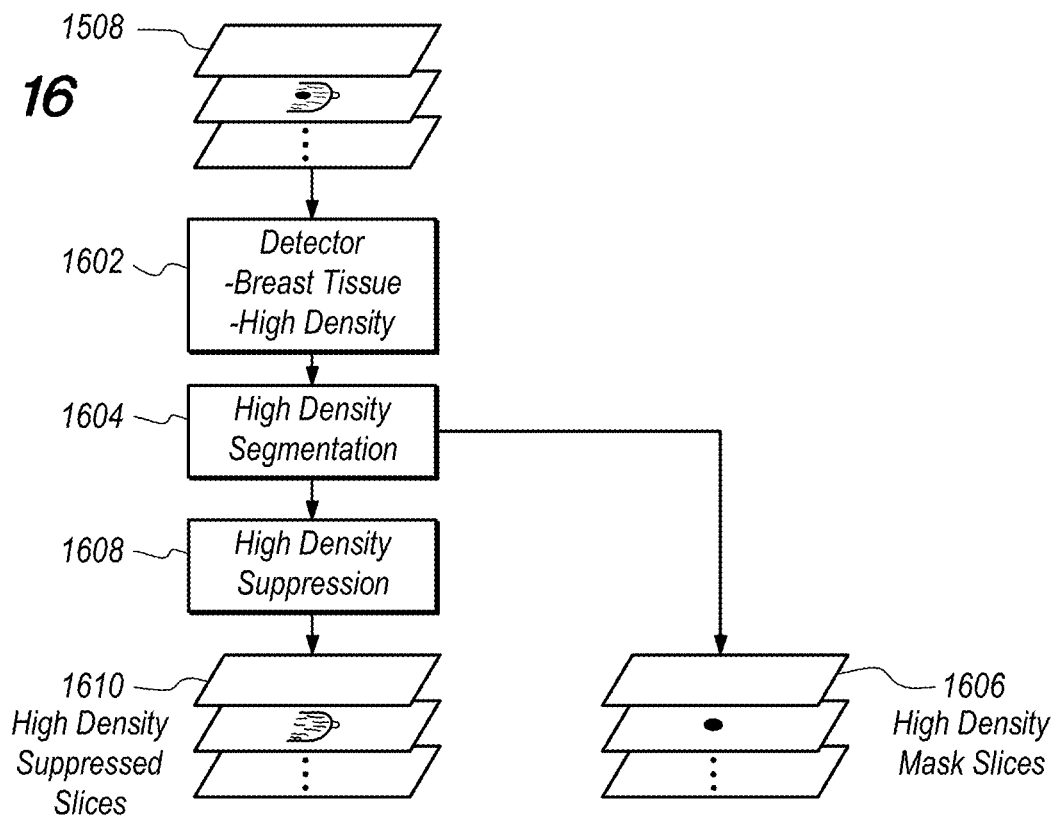
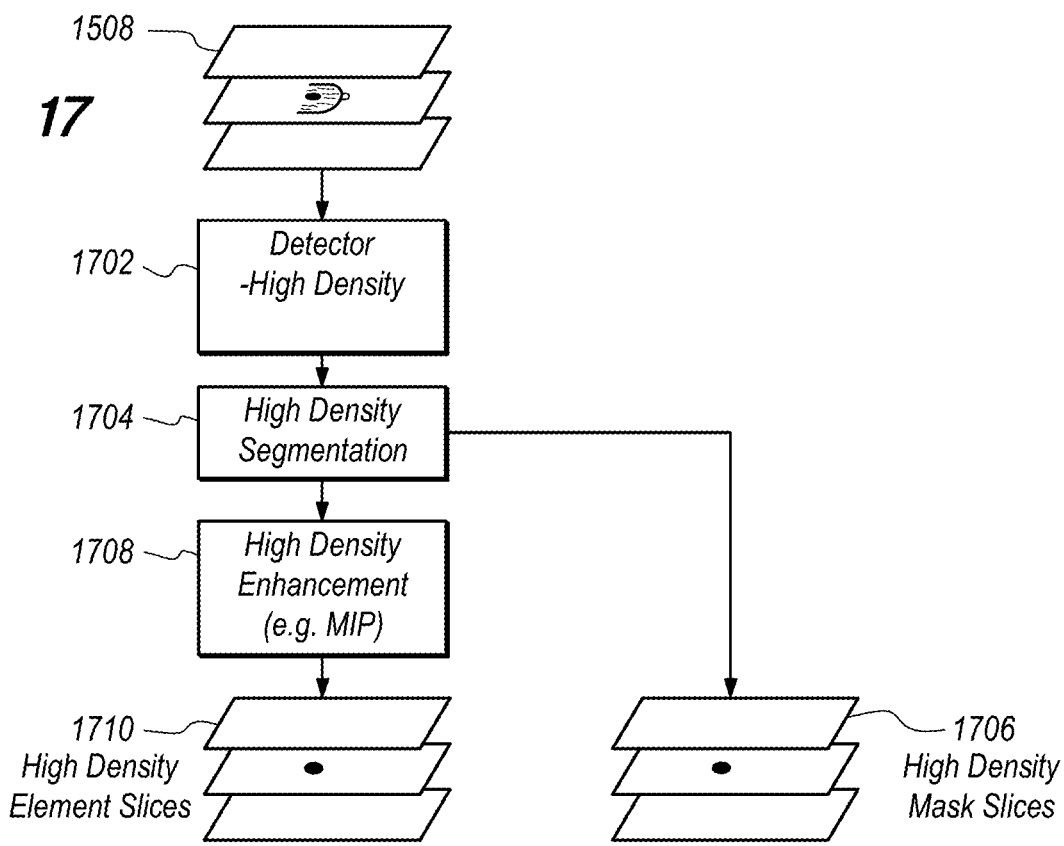

*(Multi-Flow Image Processing)*

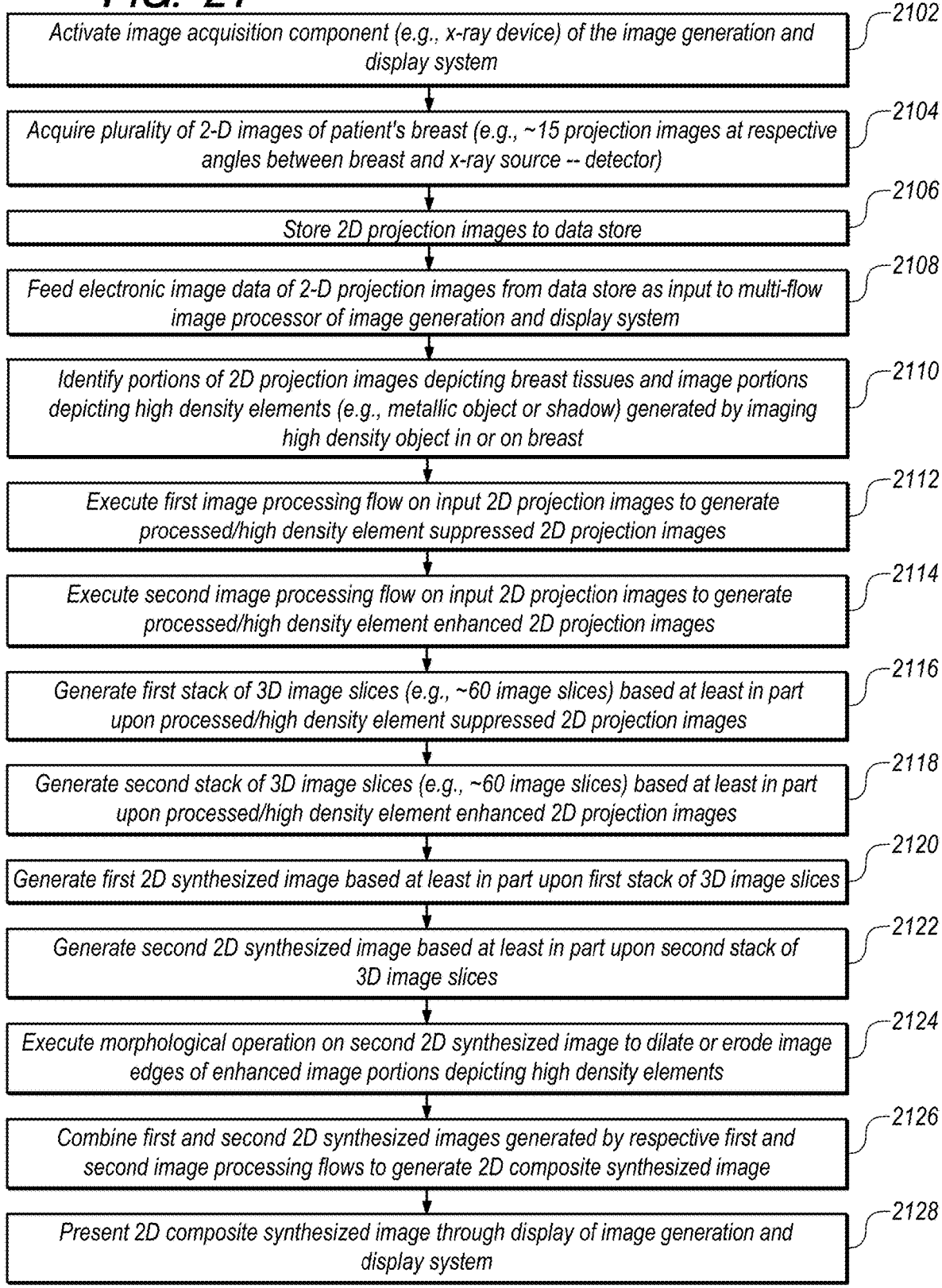

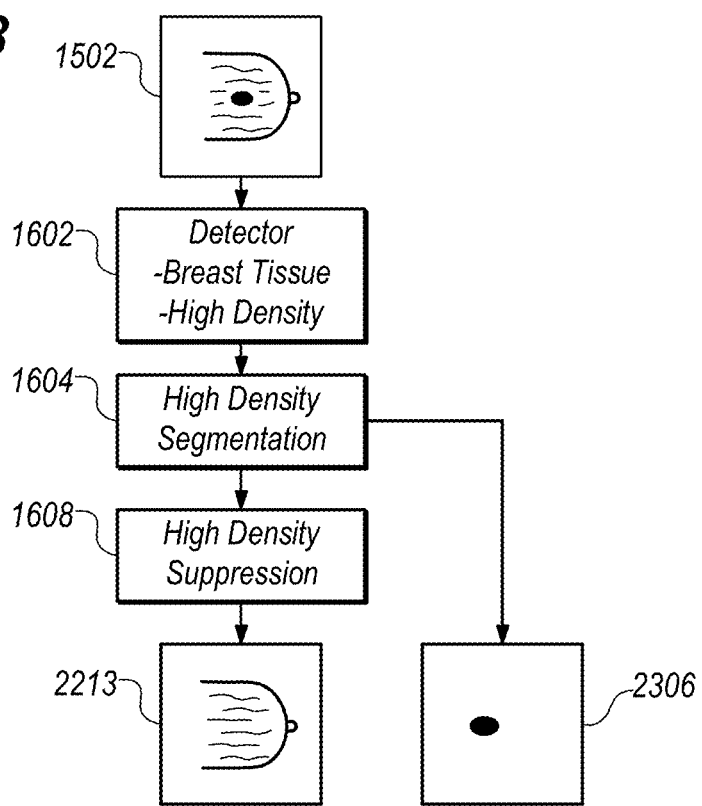
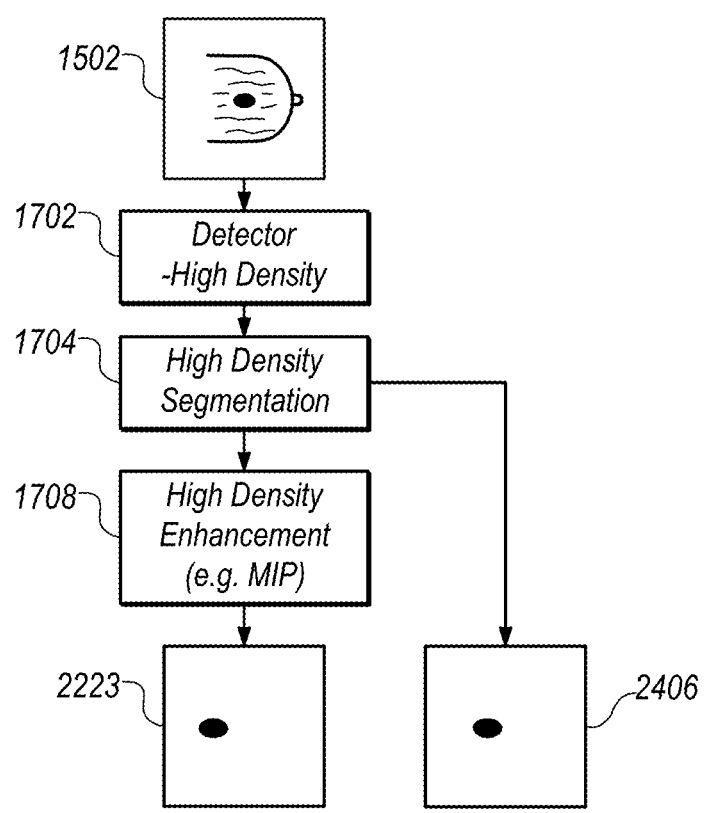

IMAGE GENERATION BY HIGH DENSITY ELEMENT SUPPRESSION

RELATED APPLICATION DATA

This application is a continuation of U.S. patent application Ser. No. 17/280,866, now U.S. Pat. No. 11,857,358, filed Mar. 26, 2021, which is a National Stage Application of PCT/US2019/052621, filed Sep. 24, 2019, which claims the benefit of U.S. Provisional Patent Application No. 62/738,244, filed Sep. 28, 2018, the entire disclosures of which are incorporated herein by reference in their entireties. To the extent appropriate, a claim of priority is made to each of the above disclosed applications.

FIELD

The presently disclosed inventions relate generally to breast imaging techniques such as tomosynthesis, and more specifically, to systems and methods for processing images of breast images that include obtrusive high density elements.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional (3D) images of the breast using methods such as breast tomosynthesis. In contrast to two-dimensional (2D) images generated by legacy mammography systems, breast tomosynthesis systems construct or generate a 3D image volume from a series of 2D projection images, each projection image obtained at a different angular displacement of an x-ray source relative to the image detector as the x-ray source is scanned over the detector. The constructed 3D image volume or stack is typically presented as a plurality of slices of image data, the slices being mathematically reconstructed on planes typically parallel to the imaging detector. The reconstructed tomosynthesis slices reduce or eliminate the problems caused by tissue overlap and structure noise present in 2D mammography imaging, by permitting a user such as a radiologist or other medical professional to scroll through the image slices to view only the structures in that slice.

Imaging systems such as tomosynthesis systems have recently been developed for breast cancer screening and diagnosis. In particular, Hologic, Inc. has developed a fused, multimode mammography/tomosynthesis system that acquires one or both types of mammogram and tomosynthesis images, either while the breast remains immobilized or in different compressions of the breast. Other companies have introduced systems that include tomosynthesis imaging; e.g., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may optionally be displayed along with tomosynthesis projection or reconstructed images, in order to assist in screening and diagnosis.

The 2D synthesized image is designed simulate a traditional 2D mammogram while not losing relevant information from tomosynthesis slices that may not be readily visible in a traditional 2D mammogram. The 2D synthesized image includes any clinically important and meaningful information, such as abnormal lesions and normal breast structures, while representing in relevant part of a traditional 2D image. There are many different types of lesions and breast structures that may be defined as different types of image objects having different characteristics. For any given image object visible in the 3D volume data, it is important to maintain and enhance the image characteristics (e.g., micro-calcifications, architectural distortions, etc.) as much as possible in the 2D synthesized image. To achieve the enhancement of the targeted image object, it is important to accurately identify and represent the image object present in the 3D tomosynthesis data.

It is also important to generate 3D volumes of reconstruction image slices and 2D synthesized images representing the 3D reconstruction image slices that clearly depict structures of interest within breast tissue while reducing or eliminating unwanted image objects and artifacts that can block or obscure objects of interest and clinically important information. For example, metallic biopsy markers are often inserted into a patient's breast so that a radiologist can readily identify the prior biopsy location during subsequent review or during following up examinations. Certain known biopsy markers are made of biocompatible metallic materials such as stainless steel, titanium or nickel titanium and can have various shapes including an expandable mesh-like or net-like structure, cylindrical bodies and twisted wires depending on the application and biopsy attributes such as size, orientation and location. Examples of biopsy markers include TUMARK, SECURMARK, TRIMARK and CELEROMARK biopsy site markers available from Hologic, Inc., Marlborough, MA.

However, in the process of generating 3D reconstruction slices and subsequent generation of a 2D synthesized image, high density objects such as metallic biopsy markers or clips may themselves obscure breast tissue of interest, and shadows generated by imaging these metallic biopsy markers may also extend or penetrate into breast tissue to obscure breast tissue image portions in various directions as a result of imaging around the breast. Imaging biopsy markers or clips and external skin markers of different shapes and sizes can introduce different shapes, sizes and numbers of shadows or imaging artifacts throughout different portions of a 3D image stack and resulting 2D synthesized image. These shadow artifacts can be difficult to work around and it may not be possible to view a particular breast tissue area of interest. These obtrusive areas reduce the quality of 2D synthesized images and may reduce the accuracy of assessments based on same since structures of interest may be blocked or obscured by high density objects and/or resulting shadows (and possibly reflections from metallic objects depending on the type of biopsy marker material and imaging system utilized).

SUMMARY

Embodiments of the disclosed inventions provide for computerized image generation and display systems and methods for eliminating or reducing imaging artifacts such as shadows generated by imaging of high density or radiopaque objects in or on breast tissue. A high density object such as a shadow is suppressed in a synthesized image to provide a clearer and more accurate of breast tissue while providing for more accurate and efficient image generation and radiologist review.

Embodiments of the disclosed inventions also provide for differential or multi-flow image processing on input breast images so that input images are processed in different ways to generate different resulting images that are combined or merged to generate a synthesized composite image. The resulting synthesized composite image has reduced or no shadow artifacts resulting from imaging high density or radiopaque objects in or on breast tissue, while other elements or aspects of the images are maintained or enhanced.

Embodiments also provide for generation of synthesized images based on image inputs of different dimensional formats. For example, in one embodiment, a 3D set of images collectively depicting breast tissue based on image data generated by a breast imaging system and depicting a high density object in or on breast tissue is processed in different ways to generate different intermediate image sets. A high density object is suppressed in a first intermediate image set and enhanced in a second intermediate image set. A two-dimensional (2D) composite synthesized image that is free of the high density object based at least in part upon the first intermediate image set and the second intermediate image set and presented through a display of the breast imaging system. In another embodiment, a 2D set of projection images rather than a 3D set of images constructed based on the 2D set of projection images is the input to the image processor and processed in different ways for high density element suppression and breast enhancement in one image processing flow and for high density element enhancement in another image processing flow. A two-dimensional (2D) composite synthesized image that is free of the high density object based at least in part upon the first intermediate image set and the second intermediate image set and presented through a display of the breast imaging system.

Another embodiment for breast tissue image data processing comprises generating a first set of images collectively depicting breast tissue based on image data generated by a breast imaging system, the first set of images depicting a high density object and processing the first set of images in different ways to generate a second set of images in which the high density object is suppressed and breast tissue is enhanced and to generate a third set of images in which the high density object is enhanced. The second set of images is processed to generate a fourth set of images in which the high density object is suppressed, and the third set of images is processed to generate a fifth set of images in which the high density object is enhanced. A composite synthesized image is generated and free of the high density object based at least in part upon the fourth set of images and the fifth set of images and presented through a display of the breast imaging system.

In one embodiment of the disclosed inventions, a 3D set or stack of image slices (e.g., generated by reconstruction of 2D projection images acquired by an x-ray imaging device of a breast imaging system) collectively depicts breast tissue and is fed as an input to a multi-flow image processor of the breast imaging system. The input 3D set of image slices is processed in different ways to generate a first 3D set of image slices in which high density objects are suppressed and breast tissue is enhanced and a second 3D set of image slices in which high density objects are enhanced. A first 2D synthesized image or first intermediate image is generated based at least in part upon or embodying enhanced tissue image portions of the first 3D set, and a second 2D synthesized image or second intermediate image is generated based at least in part upon or embodying enhanced high density object image portions of the second 3D set. The first and second 2D synthesized images are combined or merged together to generate a 2D composite synthesized image that is presented to a radiologist through a display of the image generation and display system.

According to another embodiment, multi-flow or differential image processing involving high density element suppression is applied to 2D acquired or projection images rather than on a 3D stack of image slices. In other words, the input to an image processor may be data of images of different dimensional formats and multi-flow image processing may be executed before or after image reconstruction. Thus, multi-flow or differential image processing involving high density element suppression may be executed before image reconstruction and before a 3D stack of image slices has been generated or after image reconstruction and after a 3D stack of image slices has been generated, and an image processor may receive different types and/or combinations of images, which may or may not involve reconstruction and Tr images.

In one embodiment, a breast image processing method involves acquiring a plurality of 2D images depicting breast tissue by an image acquisition component, e.g., using a radiation source and detector positioned at different angles while the breast is between the source and detector. The acquired 2D images are fed as an input to the multi-flow image processor of a breast imaging system. The image processor executes a first image processing method or flow to generate a first processed set of 2D images in which portions of the first processed set of 2D images depicting breast tissue are enhanced and other portions of the first processed set of 2D images depicting a high density element are suppressed. The image processor also executes a second image processing method different from the first image processing method to generate a second processed set of 2D images in which portions of the second set that depict high density elements are enhanced while not enhancing breast tissue. For this purpose, object enhancement modules that are utilized in the first image processing method or flow are not executed or deactivated in the second image processing method or flow. After multi-flow image processing on 2D images to generate new sets of intermediate 2D images, synthesized images may be generated and merged or combined to generate a 2D composite synthesized image, which is presented through a display of the image generation and display system. 2D synthesized images may be generated from the new sets of 2D images or from generated 3D stacks of image slices generated by reconstruction. In these embodiments, a first intermediate 3D set of image slices collectively depicting breast tissue based at least in part upon the first processed set of 2D images and a second intermediate 3D set of image slices collectively depicting breast tissue based at least in part upon the second processed set of 2D images are constructed. These 3D sets are used to generate respective first and second 2D synthesized based at least in part upon respective first and second 3D image slice sets. Thus, while certain embodiments are described with reference to 3D sets or stacks of image slices used to generate 2D synthesized images, embodiments are not so limited, and an image synthesizer can use different types and combinations of images including different combinations of Tr (tomosynthesis reconstruction images), Tp (tomosynthesis projection images) and Mp (mammography projection images). Further, Mp images can be fused into a 2D synthesized image since Mp images provide a better representation of certain image elements such as calcifications. Accordingly, an image processor including metal suppression and metal enhancement synthesizers may use one or more and different combinations of tomosynthesis reconstruction images Tr, tomosynthesis projection images Tp and mammography projection images Mp.

Embodiments may thus involve different dimensional image formats, conversions from one dimensional format to another, different types and numbers of intermediate image sets generated before generation of a 2D synthesized composite image, and image processing executed on images of different dimensional formats and particular image processing sequences involving different dimensional formats. Embodiments may involve the multi-flow image processor being executed on constructed 3D sets of image slices such that multi-flow image processing may not be executed on 2D acquired or projection images. Embodiments may involve the multi-flow image processor being executed on 2D acquired or projection images such that multi-flow image processing may not be executed on reconstructed 3D stacks of image slices. Additionally, generation of 2D synthesized images may be based on an intermediate or 3D stack of image slices constructed from 2D projection images, or generated from a 2D image without generating a 3D stack. Moreover, selective suppression in the first image processing flow may be applied to a high density element in the form of a high density or radiopaque object itself and/or a high density element in the form of an imaging artifact or shadow generated by imaging a high density object.

Yet other embodiments may involve multi-flow or differential image processing including high density element suppression executed on 2D acquired or projection images and then multi-flow or differential processing including high density element suppression executed on constructed 3D sets of image slices. Thus, high density element suppression and enhancement may be performed both before and after reconstruction to generate a 3D stack of image slices to provide a further enhanced 2D composite synthesized image.

One embodiment of a computer-implemented method for processing images of breast tissue includes feeding image data of a plurality of images of a patient's breast as an input into a multi-flow image processor of an image generation and display system. The image processor identifies portions of breast tissue images depicting breast tissue and portions of images depicting high density elements generated by imaging a high density object in or on the patient's breast (e.g., using radiation generated by a radiation source impacting on a radiation detector disposed on opposite sides of a patient's tissue). The method further comprises the image processor executing different image processing methods that may be executed in parallel and on the same image data input. A first image processing method enhances image portions depicting breast tissue while suppressing image portions depicting a high density element. For example, a high density element such as a radiopaque metal object or shadow generated thereby may be identified within an image as being a high density element using a pre-determined filter or criteria based on one or more of measured contrast and brightness or other image criteria or filter, which may also be indicative of the radiopacity of the high density element. High density element portions may be detected, segmented and suppressed by being filled in or replaced with other image background data, e.g., by interoperation or background sampling and duplication. In this manner, high density or radiopaque elements are essentially eliminated or modified and not visually perceptible in processed images. A first 3D stack of image slices embodies enhanced image portions depicting breast tissue and suppressed image portions depicting high density elements. For example, a first 3D set of image slices may be in the form of a reconstructed set of image slices in which each image represents a slice of the breast as it would appear in an image of that slice at any desired angle. The first image processing method further comprises generating a first 2D synthesized or "artificial" image based at least in part upon the first 3D set of image slices. The second image processing method is different from the first image processing method and involves enhancing, rather than suppressing, image portions depicting high density elements, and this may be performed without enhancing or emphasizing breast tissue or lesions or objects of interest thereof. Identified high density or radiopaque elements may be enhanced using one or more image filtering/processing algorithms that are designed to highlight objects with sharp contrast, examples of which include algorithms for edge enhancement, contrast enhancement and intensity projection (e.g., maximum/mean intensity projection). A second 3D set of image slices embodying enhanced image portions depicting high density elements is generated, and a second 2D synthesized image is generated based at least in part upon the second 3D set of image slices. The image processor combines or merges the first and second 2D synthesized images generated by respective first and second image processing flows to generate a composite 2D image, which is displayed to a user of the system.

In a single or multiple embodiments an acquisition component, such as an x-ray image acquisition component of the image generation and display system, is activated to acquire the plurality of images of the patient's breast. Acquired images, such as 2D projection images, may be acquired using a radiation source and detector that are positioned at different angles while the breast is between the source and detector.

In a single or multiple embodiments, image data that is fed into the image processor and on which the first and second image processing flows are executed is image data of 2D projection images. Thus, in these embodiments, high density or radiopaque element suppression of the first image processing flow is executed before image reconstruction and thus before generation of a 3D stack of image slices, and high density or radiopaque element suppression is not executed on the 3D stack of image slices.

In a single or multiple embodiments, image data fed into the image processor and on which the first and second first and second processing flows are executed is a 3D set or stack of image slices. Thus, in these embodiments, high density element suppression of the first image processing flow is executed after image reconstruction and thus after generation of a 3D stack of image slices. High density element suppression is not executed on 2D projection images.

In a single or multiple embodiments, metal suppression of the first image processing flow and metal enhancement of the second image processing flow are executed directly on the same input images, such as 2D projection images. In other embodiments, metal suppression of the first image processing method and metal enhancement of the second image processing method are executed on intermediate 3D reconstructed image slice sets but not on 2D projection images.

In a single or multiple embodiments, high density element image portions that are suppressed include a metallic or radiopaque object itself and/or shadow generated thereby.

The high density element may extend across multiple slices of the input set of 3D image slices. The metallic object may be a foreign object that is inserted into breast tissue such as a metallic biopsy marker or clip. The high density element may also be a shadow generated by imaging of the metallic biopsy marker or other foreign object. Embodiments of the inventions may also be used when processing images including a high density or radiopaque object in the form of a calcification image processing method. Thus, high density or radiopaque elements may be foreign objects or elements originating from within breast tissue. Moreover, while reference is made to such high density objects that may be radiopaque, it will be understood that such objects may indeed be radiopaque or only to a certain degree so as to not be entirely radiopaque but still obscuring breast tissue, and shadow artifacts generated by imaging a metallic object may not be radiopaque. Accordingly, a "high density element" is construed and defined to include metallic objects such as a biopsy marker or a skin marker, radiopaque materials or objects, and shadows or shadow artifacts generated by imaging of same, and embodiments may be executed to suppress some or all high density elements in an image, e.g., suppress shadows but not a biopsy marker.

With embodiments, the first imaging processing method suppresses the identified image portions depicting the high density element such that the high density element is not visible in the first 3D set of image slices or the eventually generated 2D synthesized image. In a single or multiple embodiments, the first 2D synthesized image is free of high density elements and/or shadow elements generated by imaging a high density element.

In a single or multiple embodiments, the image processing method may involve a segmentation mask that is used to generate the second 2D synthesized image in which the high density element is enhanced, and may involve a morphological operation that is executed on the second 2D synthesized image to dilate or erode image edges of enhanced image portions depicting high density elements to increase the sharpness thereof. For example, the second image processing method may involve segmenting image portions identified as depicting high density elements to determine respective pixel data or values of segmented image portions, and generating a high density element mask based on respective pixel data or values. The mask may be a binary pixel level mask—"1" for pixels of high density elements, and "0" for other pixels. The mask may be subsequently utilized by the image processor to determine which portions of the second 2D synthesized image to include in the 2D synthesized image when merging or combining the first two-dimensional synthesized image and the second two-dimensional synthesized image, e.g., by modulated combination of the first 2D synthesized image and the second 2D synthesized image utilizing the high density element mask.

In a single or multiple embodiments, high density element suppression of the first image processing method is executed by interpolation over the image portions depicting the high density element, replacing high density element pixels with sampled breast tissue or background pixels that are not enhanced.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIG. 16 illustrates an image-flow diagram of breast tissue enhancement and high density suppression of a first image processing flow in which high density elements are suppressed and breast tissue elements are enhanced;

FIG. 17 illustrates an image-flow diagram of high density element enhancement of a second image processing flow in which high density elements are enhanced;

FIG. 21 illustrates a flow diagram of multi-flow or differential image processing that is executed directly on an input 2D images;

FIG. 23 illustrates an image-flow diagram of breast tissue enhancement and high density suppression of a first image processing flow executed by a multi-flow image processor that executes on 2D image inputs and during which high density elements are suppressed and breast tissue elements are enhanced; and FIG. 24 illustrates an image-flow diagram of high density element enhancement of a second image processing flow of a multi-stage image processor that executes on 2D image inputs and during which high density elements are enhanced.

DETAILED DESCRIPTION OF THE ILLUSTRATED EMBODIMENTS

Figure 1:
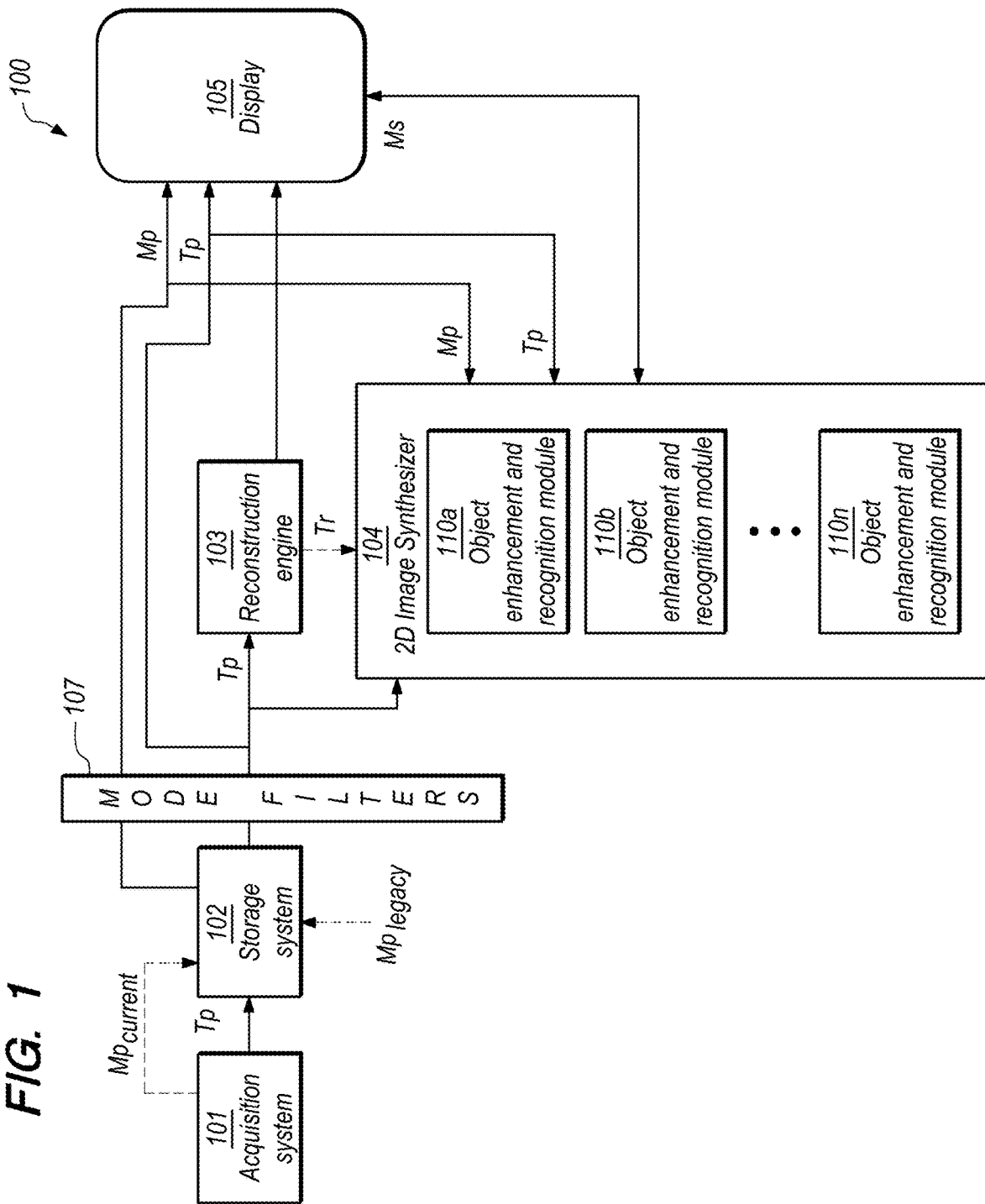
FIG. 1 is a block diagram illustrating the flow of data through an exemplary breast image acquisition and processing system in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

An "acquired image" refers to an image generated while visualizing a patient's tissue. Acquired images can be generated by radiation from a radiation source impacting on a radiation detector disposed on opposite sides of a patient's tissue, as in a conventional mammogram.

A "reconstructed image" refers to an image generated from data derived from a plurality of acquired images. A reconstructed image simulates an acquired image not included in the plurality of acquired images.

A "synthesized image" refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

An "Mp" image is a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

A "Tp" image is an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display, storage, and/or other use.

A "Tr" image is a type (or subset) of a reconstructed image that is reconstructed from tomosynthesis projection images Tp, for example, in the manner described in one or more of U.S. Pat. Nos. 7,577,282, 7,606,801, 7,760,924, and 8,571,289, the disclosures of which are fully incorporated by reference herein in their entirety, wherein a Tr image represents a slice of the breast as it would appear in a projection x ray image of that slice at any desired angle, not only at an angle used for acquiring Tp or Mp images.

An "Ms" image is a type (or subset) of a synthesized image, in particular, a synthesized 2D projection image that simulates mammography images, such as a craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-incorporated U.S. Pat. Nos. 7,760,924 and 8,571,289 and also U.S. application Ser. No. 15/120,911, published as U.S. Publication No. 2016/0367120 on Dec. 22, 2016 and entitled System and Method for Generating and Displaying Tomosynthesis Image Slabs, PCT Application No. PCT/US2018/024911, filed Mar. 28, 2018 and entitled System and Method for Hierarchical Multi-Level Feature Image Synthesis and Representation, PCT Application No. PCT/US2018/024912, filed Mar. 28, 2018, and entitled System and Method for Synthesizing Low-Dimensional Image Data From High-Dimensional Image Data Using an Object Grid Enhancement, and PCT Application No. PCT/US018/0249132, filed Mar. 28, 2018, and entitled System and Method for Targeted Object Enhancement to Generate Synthetic Breast Tissue Images, the contents of all of which are incorporated herein by reference as thought set forth in full.

It should be appreciated that Tp, Tr, Ms and Mp image data encompasses information, in whatever form, that is sufficient to describe the respective image for display, further processing, or storage. The respective Mp, Ms. Tp and Tr images, including those subjected to high density element suppression and enhancement, are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In a preferred embodiment, the geometry of the tomosynthesis images (Tr and Tp) and mammography images (Ms and Mp) are matched to a common coordinate system, as described in U.S. Pat. No. 7,702,142. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

The term "high density element" is defined as an element, when imaged with breast tissue, partially or completely obscures imaged breast tissue or clinically important information of breast tissue such as malignant breast mass, tumors, etc. A high density element may be detected based on pre-determined criteria or filters involving one or more of contrast, brightness, radiopacity or other attribute. A high density element may be a foreign object or naturally occurring within breast tissue and may be partially or completely radiopaque. For example, one type of high density element is a metallic object such as a metallic biopsy marker inserted into breast tissue. Such markers are designed to be radiopaque such that they are clearly visible when using x-rays. Another example of a high density element is a calcification within the breast tissue. A high density element may also be a non-metallic or non-calcified element such as a shadow artifact generated by imaging a metallic marker, and which may not be considered to be radiopaque. Accordingly, a "high density element" is defined to include metallic objects such as a biopsy marker or a skin marker, radiopaque materials or objects, and shadows or shadow artifacts generated by imaging of same.

The terms "differential" or "multi-flow" image processing are defined to refer to the input images being processed in different ways to generate different image results and is defined to include one flow involving suppression of an imaged high density element and involving enhancement of an imaged high density element. Different image processing flows can be executed in parallel and simultaneously, and images input to image processors of embodiments may be of different dimensional formats.

In order to ensure that a synthesized 2D image displayed to a reviewer or end-user (e.g., an Ms image) includes the most clinically relevant information, it is necessary to detect and identify 3D objects, such as malignant breast mass, tumors, etc., within the breast tissue. Towards this end, in accordance with embodiments of the presently disclosed inventions, 3D objects may be identified using multiple target object recognition/synthesis modules, wherein each target recognition/synthesis module may be configured to identify and reconstruct a particular type of object. These multiple target synthesis modules may work together in combining information pertaining to respective objects during the reconstruction process of generating one or more synthesized 2D images, ensuring that each object is represented accurately, and preserving clinically significant information on the 2D synthesized images that are the displayed to the end-user.

The synthesized 2D image that is displayed to an end-user should also be clear such that clinically relevant information and objects are not obscured by undesirable image elements or artifacts, which may include a high density element such as a biopsy marker and/or a shadow generated by imaging of same during breast imaging. Towards this end, in accordance with embodiments of the presently disclosed inventions, a multi-flow image processor is utilized to generate a 2D synthesized image by suppressing high density elements in one image processing method and enhancing high density elements in another image processing method such that when different 2D synthesized images generated by different image processing flows are combined, high density elements such as shadows are reduced or eliminated resulting in a composite 2D synthesized image that is clearer and more accurately depicts breast tissue and breast tissue objects while providing for more accurate and efficient radiologist review.

Embodiments designed to generate a 2D synthesized image that maintains and enhances clinically interesting characteristics are described with reference to FIGS. 1-8B, and embodiments that utilize a multi-flow image processing method for reducing of high density elements such as shadows and generate a clearer 2D composite synthesized image are described with reference to FIGS. 9-24.

FIG. 1 illustrates the flow of data in an exemplary image generation and display system 100, which incorporates each of synthesized image generation, object identification, and display technology. It should be understood that, while FIG. 1 illustrates a particular embodiment of a flow diagram with certain processes taking place in a particular serial order or in parallel, the claims and various other embodiments described herein are not limited to the performance of the image processing steps in any particular order, unless so specified.

More particularly, the image generation and display system 100 includes an image acquisition system 101 that acquires tomosynthesis image data for generating Tp images of a patient's breasts, optionally using the respective 3D and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend "$Mp_{legacy}$" in FIG. 1) in a storage device 102, which is preferably a DICOM-compliant Picture Archiving and Communication System (PACS) storage device. Following acquisition, the tomosynthesis projection images Tp may also be transmitted to the storage device 102 (as shown in FIG. 1). The storage device 102 may further store a library of known 3D objects that may be used to identify significant 3D image patterns to the end-user. In other embodiments, a separate dedicated storage device (not shown) may be used to store the library of known 3D objects with which to identify 3D image patterns or objects.

The Tp images are transmitted from either the acquisition system 101, or from the storage device 102, or both, to a computer system configured as a reconstruction engine 103 that reconstructs the Tp images into reconstructed image "slices" Tr, representing breast slices of selected thickness and at selected orientations, as disclosed in the above-incorporated patents and applications.

Mode filters 107 are disposed between image acquisition and image display. The filters 107 may additionally include customized filters for each type of image (i.e., Tp, Mp, and Tr images) arranged to identify and highlight or enhance certain aspects of the respective image types. In this manner, each imaging mode can be tuned or configured in an optimal way for a specific purpose. For example, filters programmed for recognizing objects across various 2D image slices may be applied in order to detect image patterns that may belong to a particular high-dimensional objects. The tuning or configuration may be automatic, based on the type of the image, or may be defined by manual input, for example through a user interface coupled to a display. In the illustrated embodiment of FIG. 1, the mode filters 107 are selected to highlight particular characteristics of the images that are best displayed in respective imaging modes, for example, geared towards identifying objects, highlighting masses or calcifications, identifying certain image patterns that may be constructed into a 3D object, or for creating 2D synthesized images (described below). Although FIG. 1 illustrates only one mode filter 107, it should be appreciated that any number of mode filters may be utilized in order to identify structures of interest in the breast tissue.

The imaging and display system 100 further includes a 2D image synthesizer 104 that operates substantially in parallel with the reconstruction engine 103 for generating 2D synthesized images using a combination of one or more input Tp (tomosynthesis projection), Mp (mammography projection), and/or Tr (tomosynthesis reconstruction) images. The 2D image synthesizer 104 consumes a set of input images, determines a set of most relevant features from each of the input images, and outputs one or more synthesized 2D images. The synthesized 2D image represents a consolidated synthesized image that condenses significant portions of various slices onto one image. This provides an end-user (e.g., medical personnel, radiologist, etc.) with the most clinically-relevant image data in an efficient manner, and reduces time spent on other images that may not have significant data.

One type of relevant image data to highlight in the synthesized 2D images would be relevant objects found across one or more Mp, Tr and/or Tp images. Rather than simply assessing image patterns of interest in each of the 2D image slices, it may be helpful to determine whether any of the 2D image patterns of interest belong to a larger high-dimensional structure, and if so, to combine the identified 2D image patterns into a higher-dimensional structure. This approach has several advantages, but in particular, by identifying high-dimensional structures across various slices/depths of the breast tissue, the end-user may be better informed as to the presence of a potentially significant structure that may not be easily visible in various 2D slices of the breast.

Further, instead of identifying similar image patterns in two 2D slices (that are perhaps adjacent to each other), and determining whether or not to highlight image data from one or both of the 2D slices, identifying both image patterns as belonging to the same high-dimensional structure may allow the system to make a more accurate assessment pertaining to the nature of the structure, and consequently provide significantly more valuable information to the end-user. Also, by identifying the high-dimensional structure, the structure can be more accurately depicted on the synthesized 2D image. Yet another advantage of identifying high-dimensional structures within the various captured 2D slices of the breast tissue relates to identifying a possible size/scope of the identified higher-dimensional structure. For example, once a structure has been identified, previously unremarkable image patterns that are somewhat proximate to the high-dimensional structure may now be identified as belonging to the same structure. This may provide the end-user with an indication that the high-dimensional structure is increasing in size/scope.

To this end, the 2D image synthesizer 104 employs a plurality of target object recognition/enhancement modules (also referred to as target object synthesis modules) that are configured to identify and reconstruct different types of objects. Each target image recognition/synthesis module may be applied (or "run") on a stack (e.g., a tomosynthesis image stack) of 2D image slices of a patient's breast tissue, and work to identify particular types of objects that may be in the breast tissue, and ensure that such object(s) are represented in a clinically-significant manner in the resulting 2D synthesized image presented to the end-user. For example, a first target image synthesis module may be configured to identify calcifications in the breast tissue. Another target image synthesis module may be configured to identify and reconstruct spiculated lesions in the breast tissue. Yet another target image synthesis module may be configured to identify and reconstruct spherical masses in the breast tissue. In one or more embodiments, the multiple target image synthesis modules process the image slice data and populate respective objects in a high-dimensional grid (e.g., 3D grid) comprising respective high-dimensional structures (e.g., 3D objects) present in the breast tissue. This high-dimensional grid may then be utilized to accurately depict the various structures in the 2D synthesized image.

A high-dimensional object may refer to any object that comprises at least three or more dimensions, e.g., 3D or higher object, or a 3D or higher object and time dimension, etc. Examples of such objects or structures include, without limitation, calcifications, spiculated lesions, benign tumors, irregular masses, dense objects, etc. An image object may be defined as a certain type of image pattern that exists in the image data. The object may be a simple round object in a 3D space, and a corresponding flat round object in a 2D space. It can be an object with complex patterns and complex shapes, and it can be of any size or dimension. The concept of an object may extend past a locally bound geometrical object. Rather, the image object may refer to an abstract pattern or structure that can exist in any dimensional shape. It should be appreciated that the inventions disclosed herein are not limited to 3D objects and/or structures, and may include higher-dimensional structures. It should be appreciated that each of the target image synthesis modules is configured for identifying and reconstructing respective types of objects. These "objects" may refer to 2D shapes, 2D image patterns, 3D objects, or any other high-dimensional object, but in any event will all be referred to as "objects" or "3D objects" herein for simplicity, but this illustrative use should not be otherwise read as limiting the scope of the claims.

In the illustrated embodiment, the 2D synthesizer 104 comprises a plurality of target object recognition/enhancement modules (e.g., 110a, 110b . . . 110n), each configured for recognizing and enhancing a particular type of object. Each of the target object recognition/enhancement modules 110 may be run on a 2D image stack (e.g., Tr image stack), and is configured to identify the respective object (if any is/are present) therein. By identifying the assigned object in the 2D image stack, each target object recognition/enhancement module 110 works to ensure that the respective object is preserved and depicted accurately in the resulting 2D synthesized image presented to the end-user.

In some embodiments, a hierarchical model may be utilized in determining which objects to emphasize or de-emphasize in the 2D synthesized image based on a weight or priority assigned to the target object recognition/enhancement module. In other embodiments, all objects may be treated equally, and different objects may be fused together if there is an overlap in the z direction, as will be discussed in further detail below. These reconstruction techniques allow for creation of 2D synthesized images that comprise clinically-significant information, while eliminating or reducing unnecessary or visually confusing information.

The synthesized 2D images may be viewed at a display system 105. The reconstruction engine 103 and 2D image synthesizer 104 are preferably connected to a display system 105 via a fast transmission link. The display system 105 may be part of a standard acquisition workstation (e.g., of acquisition system 101), or of a standard (multi-display) review station (not shown) that is physically remote from the acquisition system 101. In some embodiments, a display connected via a communication network may be used, for example, a display of a personal computer or of a so-called tablet, smart phone or other hand-held device. In any event, the display 105 of the system is preferably able to display respective Ms, Mp, Tr, and/or Tp images concurrently, e.g., in separate side-by-side monitors of a review workstation, although the invention may still be implemented with a single display monitor, by toggling between images.

Thus, the imaging and display system 100, which is described as for purposes of illustration and not limitation, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 100 employs software to convert (i.e., reconstruct) tomosynthesis images Tp into images Tr, software for synthesizing mammogram images Ms, software for decomposing 3D objects, software for creating feature maps and object maps. An object of interest or feature in a source image may be considered a 'most relevant' feature for inclusion in a 2D synthesized image based upon the application of the object maps along with one or more algorithms and/or heuristics, wherein the algorithms assign numerical values, weights or thresholds, to pixels or regions of the respective source images based upon identified/detected objects and features of interest within the respective region or between features. The objects and features of interest may include, for example, spiculated lesions, calcifications, and the like.

Figure 2:
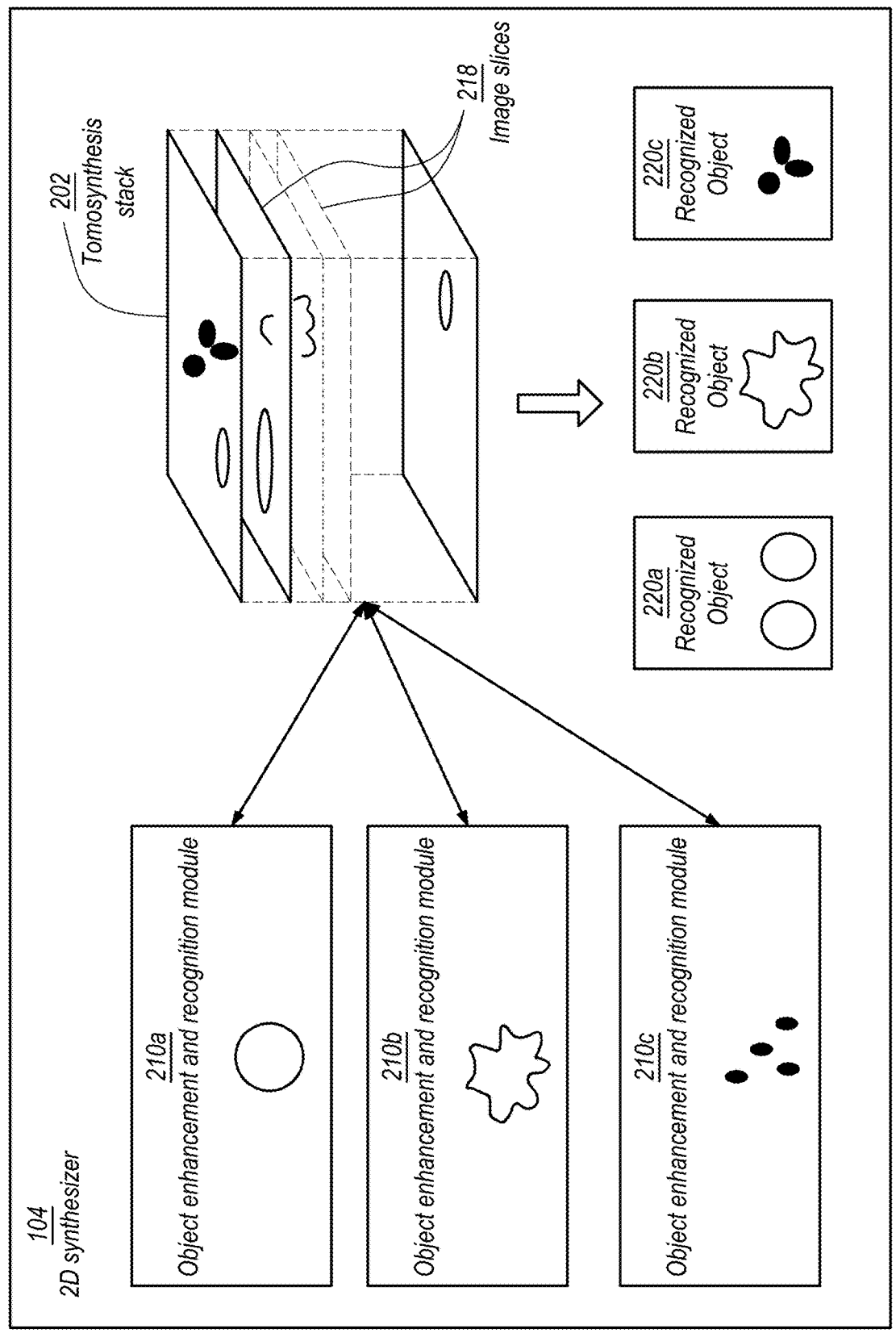
FIG. 2 is a block diagram illustrating the flow of data through a 2D synthesizer that utilizes multiple target object recognition/enhancement modules to identify respective objects in an image stack in accordance with embodiments of the disclosed inventions.

FIG. 2 illustrates the 2D image synthesizer 104 in further detail. As discussed above, various image slices 218 of a 3D tomosynthesis data set or "stack" 202 (e.g., filtered and/or unfiltered Tr and/or Tp images of a patient's breast tissue) are input into the 2D image synthesizer 104, and then processed to determine portions of the images to highlight in a synthesized 2D image that will be displayed on the display 105. The image slices 218 may be consecutively-captured cross-sections of a patient's breast tissue. Or, the image slices 218 may be cross-sectional images of the patient's breast tissue captured at known intervals. The 3D tomosynthesis stack 202 comprising the image slices 218 may be forwarded to the 2D image synthesizer 104, which evaluates each of the source images in order to (1) identify various types of objects (Tr) for possible inclusion in one or more 2D synthesized images, and/or (2) identify respective pixel regions in the images that contain the identified objects.

As shown in the illustrated embodiment, the 3D tomosynthesis stack 202 comprises a plurality of images 218 taken at various depths/cross-sections of the patient's breast tissue. Some of the images 218 in the 3D tomosynthesis stack 202 comprise 2D image patterns. Thus, the tomosynthesis stack 202 comprises a large number of input images containing various image patterns within the images of the stack.

More particularly, as shown in FIG. 2, three target object recognition/enhancement modules 210a, 210b and 210c are configured to run on the 3D tomosynthesis stack 202, wherein each of the target object recognition and enhancement modules 210 corresponds to a respective set of programs/rules and parameters that define a particular object, and how to identify that particular object amongst other objects that may exist in the breast tissue depicted by the 3D tomosynthesis stack 202. For example, filtering/image recognition techniques and various algorithms/heuristics may be run on the 3D tomosynthesis stack 202 in order to identify the object assigned to the particular target object recognition/enhancement module 210. It will be appreciated that there are many ways to recognize objects using a combination of image manipulation/filtration techniques.

For the purposes of illustration, it will be assumed that the each of the target object recognition/enhancement modules 210 identifies at least one respective object, but it should be appreciated that in many cases no objects will be identified. However, even healthy breast tissue may have one or more suspicious objects or structures, and the target object recognition/enhancement modules may inadvertently identify a breast background object. For example, all breast linear tissue and density tissue structures can be displayed as the breast background object. In other embodiments, "healthy" objects such as spherical shapes, oval shapes, etc., may simply be identified by one or more of the target object recognition/enhancement modules 210. The identified 3D objects may then be displayed on the 2D synthesized image 206; of course, out of all identified 2D objects, more clinically-significant objects may be prioritized/enhanced when displaying the respective objects on the 2D synthesized image, as will be discussed in further detail below.

In the illustrated embodiment, a first target object recognition/enhancement module 210a is configured to recognize circular and/or spherical shapes in the images 218 of the 3D tomosynthesis stack 202 (e.g., Tr, Tp, etc.). A second target object synthesis module 210b is configured to recognize lobulated shapes. A third target object synthesis module 210c is configured to recognize calcification patterns. In particular, each of the target object synthesis modules 210a,

210*b* and 210*c* is run on the Trimage stack 202, wherein a set of features/objects are recognized by the respective target object synthesis modules.

For example, target object recognition/enhancement module 210*a* may recognize one or more circular shapes and store these as "recognized objects" 220*a*. It will be appreciated that multiple image slices 218 of the 3D tomosynthesis stack 202 may contain circular shapes, and that these shapes may be associated with the same spherical object, or may belong to different spherical objects. In the illustrated embodiment, at least two distinct circular objects are recognized by the target object recognition/enhancement module 210*a*.

Similarly, target object recognition/enhancement module 210*b* may recognize one or more lobulated shapes and store these as recognized objects 220*b*. In the illustrated embodiment, one lobulated object has been recognized in the 3D tomosynthesis stack 202 by the target object recognition/enhancement module 210*b*. As can be seen, two different image slices 218 in the 3D tomosynthesis stack 202 depict portions of the lobulated object, but the respective portions are recognized as belonging to a single lobulated object by the recognition/enhancement module 210*b*, and stored as a single recognized object 220*b*.

Finally, target object recognition/enhancement module 210*c* may recognize one or more calcification shapes and store these as recognized objects 220*c*. In the illustrated embodiment, a (single) calcification cluster has been recognized by the target object recognition/enhancement module 210*c* and stored as a recognized object 220*c*. The recognized objects 220*a*, 220*b* and 220*c* may be stored at storage facilities corresponding to the respective target object recognition/enhancement modules 210*a*, 210*b* and 210*c*, or alternatively at a separate (i.e., single) storage facility that may be accessed by each of the target object recognition/enhancement modules.

Figure 3:
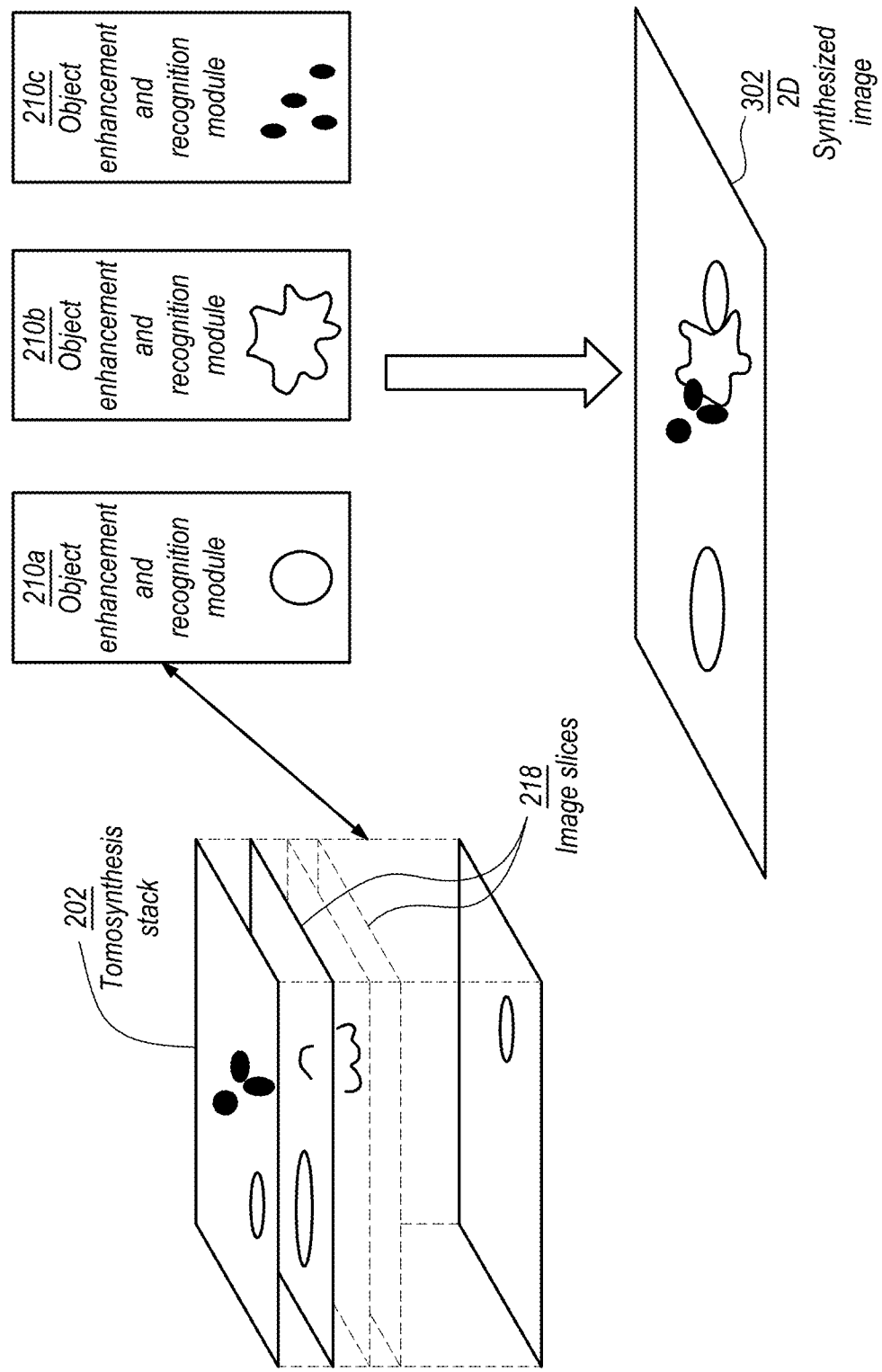
FIG. 3 illustrates one embodiment of applying target object recognition/enhancement modules on an image stack to recognize respective objects and reduce the objects onto the 2D synthesized image.

Referring now to FIG. 3, each of the target object recognition/enhancement modules 210 may be configured to identify and synthesize (e.g., to reduce to 2D) a respective 3D object to be displayed on the one or more 2D synthesized images. In other words, once the 3D objects are recognized by the respective target object recognition/enhancement module 210*a*, 210*b* or 210*c*, the target object recognition/enhancement module thereafter converts the recognized 3D object into a 2D format so that the recognized object may be displayed on the 2D synthesized image. In the illustrated embodiment, the target object recognition/enhancement modules 210*a*, 21*b* and 210*c* recognize respective objects, and convert the recognized objects into respective 2D formats. As part of the conversion process, certain of the recognized objects may be enhanced to a greater or lesser degree for the displayed image, as will be discussed in further detail below. Assuming all three target object recognition/enhancement modules 210*a*, 210*b* and 210*c* are considered equally important to the 2D image synthesizer 104, the respective 2D formats of all recognized objects (e.g., two spherical objects, one lobular object, and one calcification mass) depicted on the 2D synthesized image 302.

Figure 4:
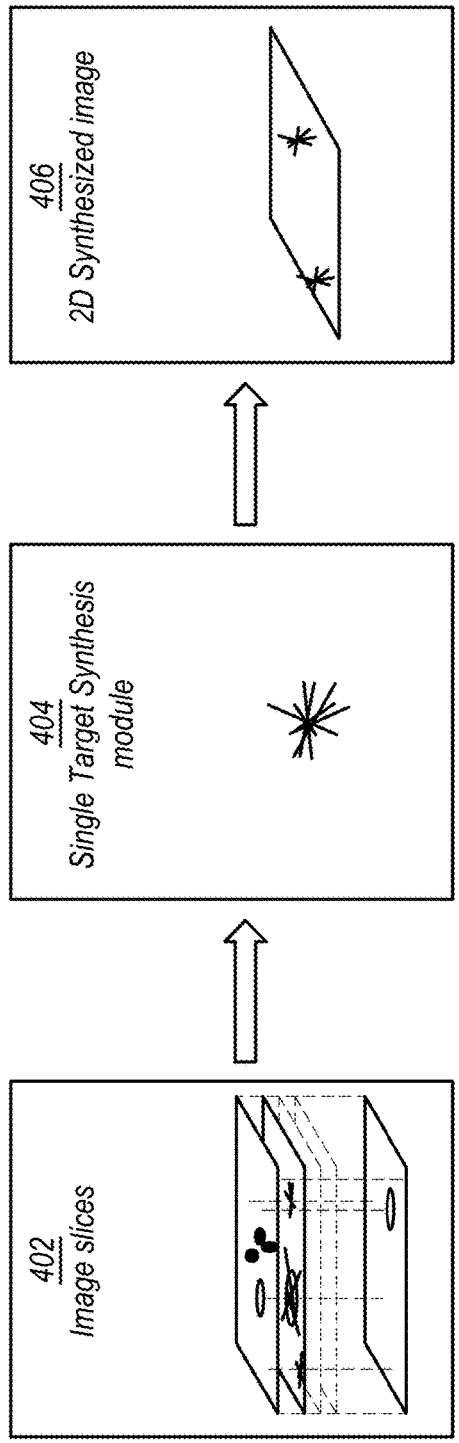
FIG. 4 illustrates a flow of data when applying a single target object recognition/enhancement module on an image stack.

FIG. 4 illustrates how a single target object recognition/enhancement module 210 may be run on a 3D tomosynthesis stack to generate a portion of the 2D synthesized image. In the illustrated embodiment, image slices 402 of the 3D tomosynthesis stack are fed through a single target object recognition/enhancement module 404, which is configured to recognize star shaped objects in the stack of images 402. As a result, the single target object synthesis module reduces information pertaining to the recognized star shape gained from various depths of the image slices onto a single 2D synthesized image 406.

Figure 5:
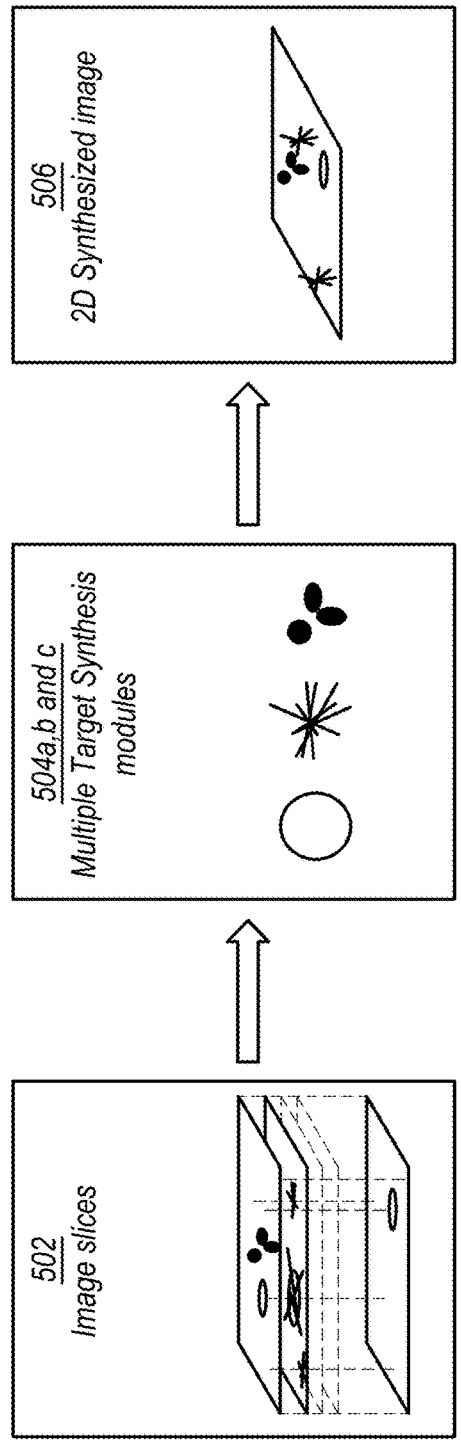
FIG. 5 illustrates a flow of data when applying multiple target object recognition/enhancement modules on an image stack.

FIG. 5 illustrates an exemplary embodiment for having multiple target object recognition/enhancement modules work together to produce the 2D synthesized image. In the illustrated embodiment, image slices 502 (of a respective 3D tomosynthesis stack) are fed through a first target object recognition/enhancement module 504*a* configured to recognize and reconstruct circular and/or spherical shapes, a second target object recognition/enhancement module 504*b* configured to recognize and reconstruct star-like shapes, and a third target object recognition/enhancement module 504*c* configured to recognize and reconstruct calcification structures. It should be appreciated that any number of target object recognition/enhancement modules may be programmed for any number of object types.

Each of the target object recognition/enhancement modules 504*a*, 504*b* and 504*c* corresponds to respective algorithms that are configured with various predetermined rules and attributes that enable these programs to successfully recognize respective objects, and reduce the recognized objects to a 2D format. By applying all three target object recognition/synthesis modules 504*a*, 504*b* and 504*c* to the image slices 502, a 2D synthesized image 506 is generated. In particular, rather than simply displaying a single type of object, the 2D synthesized image 506 comprises all three object types that are recognized and synthesized by the three target object recognition/enhancement modules 504*a*, 504*b* and 504*c*, with each of the recognized objects being equally emphasized. While this may be desirable if all the object types are of equal significance, it may be helpful to enhance/emphasize different object types to varying degrees based on their weight/priority. This technique may be more effective in alerting the end-user to a potentially important object, while de-emphasizing objects of lesser importance.

Figure 6A:
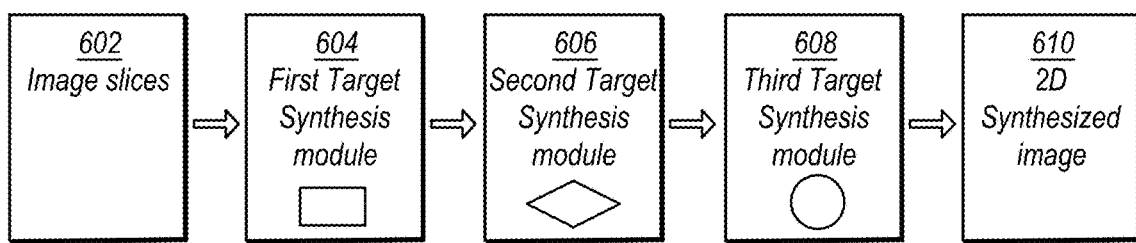
FIGS. 6A and 6B illustrate a sequential combination technique of combining data from multiple target object synthesis modules.

Referring now to FIG. 6A, a hierarchical sequential approach to combine data from the multiple target object recognition/enhancement modules is illustrated. In particular, a sequential combination technique may be applied if the various object types have a clearly defined hierarchy associated with them. For example, one type of object (e.g., spiculated lesions) may be deemed to be more clinically significant than another type of object (e.g., a spherical mass in breast tissue). This type of object (and the corresponding target object module) may be assigned a particular high weight/priority. In such a case, if two objects are competing for space on the 2D synthesized image, the object type associated with the higher priority may be emphasized/displayed on the 2D synthesized image, and the other object type may be de-emphasized, or not displayed at all. Similarly, in such an approach, each of the target object recognition/enhancement modules may be assigned respective weights based on respective significance.

In the illustrated embodiment, the image slices 602 of the 3D tomosynthesis stack are sequentially fed through three different target object recognition/enhancement modules (604, 606 and 608) to generate the 2D synthesized image 610, wherein each of the target object synthesis modules is configured to recognize and reconstruct a particular type of object. The first target object recognition/enhancement module 604 (associated with a square-shaped object) is run first on the reconstruction image slices 602, followed by the second target object recognition/enhancement module 606 (associated with a diamond-shaped object), and then followed by the third target object recognition/enhancement module 608 (associated with a circular-shaped object). It should be appreciated that since the target object recognition/enhancement modules are applied (or "run") sequentially, the second target object recognition/enhancement module 606 may be considered a higher priority object as compared with the first target object recognition/enhancement module 604, and the third target object recognition/enhancement module 608 may be considered as having a higher priority as compared to the second target object recognition/enhancement module 606. Thus, the third object type may override (or be emphasized over) the second object type, and the second object type may override (or be emphasized over) the first object type.

Figure 6B:
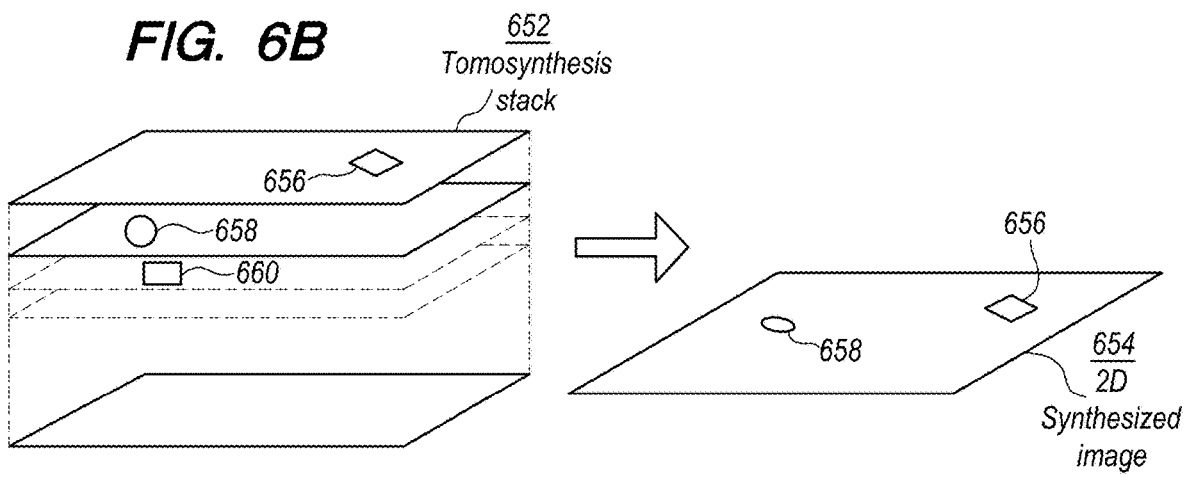

FIG. 6B illustrates this hierarchical approach to combining various object types sequentially. In particular, the 3D tomosynthesis image stack 652 includes objects 656, 658 and 660 that can be recognized in various image slices. As illustrated, objects 658 and 660 somewhat overlap in the z direction, which means that they are likely to compete for representation in the 2D synthesized image 654. When using the sequential approach of FIG. 6A to combine data from the multiple target object recognition/enhancement modules 604, 606 and 608, the programmed hierarchy is preserved. Thus, since target object recognition/enhancement module 608 configured to recognize and reconstruct circular-shaped objects has higher priority as compared to target object recognition/enhancement module 604 configured to recognize and reconstruct square-shaped objects, in a case of overlap between the two objects (as is the case in FIG. 6B), circular-shaped object 658 overrides square-shaped object 660 in the 2D synthesized image 654. Of course, it should be appreciated that since diamond-shaped object 656 does not overlap in the z direction with the other two objects, diamond shaped object 656 is also displayed in the 2D synthesized image 654. In other embodiments, instead of completing overriding the lower-priority object, the object with high-priority may be emphasized relative to the lower-priority object (rather than be omitted from display).

Figure 7A:
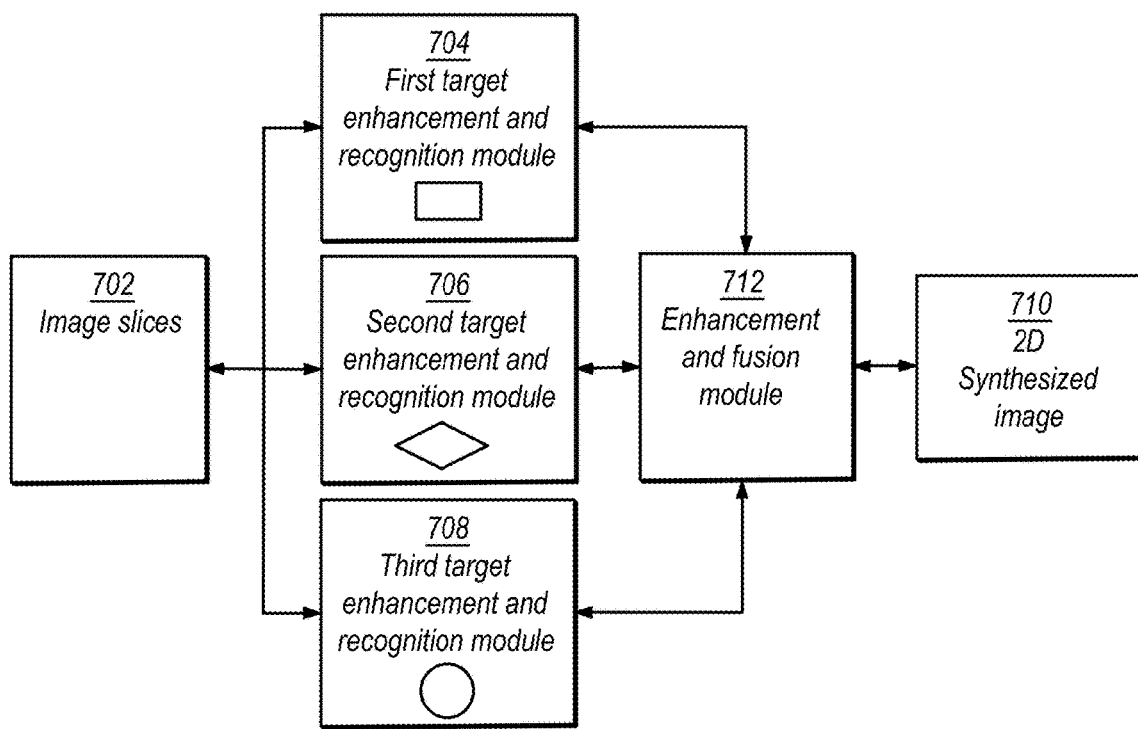
FIGS. 7A and 7B illustrate a parallel combination technique of combining data from multiple target object synthesis modules.

Another approach to running multiple target object synthesis modules on a set of image slices is illustrated in FIG. 7A. As can be seen, rather than running the multiple target object recognition/enhancement modules sequentially with the last-run target object synthesis module having the highest priority, all the target object recognition/enhancement modules may be applied in parallel. In particular, one or more enhancement or fusion modules 712 may be utilized to ensure that the various objects are combined appropriately on the 2D synthesized image. This approach may not follow a hierarchical approach, and all of the objects may be given equal weight.

The image slices 702 are fed through three different target object recognition/enhancement modules, 704, 706 and 708, in parallel. The first target object recognition/enhancement module 604 (associated with square-shaped object), the second target object recognition/enhancement module 606 (associated with diamond-shaped object), and the third target object recognition/enhancement module 608 (associated with circular-shaped object) are all run in parallel on the image slices 702. In some embodiments, an enhancement and fusion module 712 may be utilized to ensure that the different objects are fused together appropriately in case of overlap between multiple objects. The target object recognition/enhancement modules 704, 706 and 708, run in parallel may generate the 2D synthesized image 710.

Figure 7B:
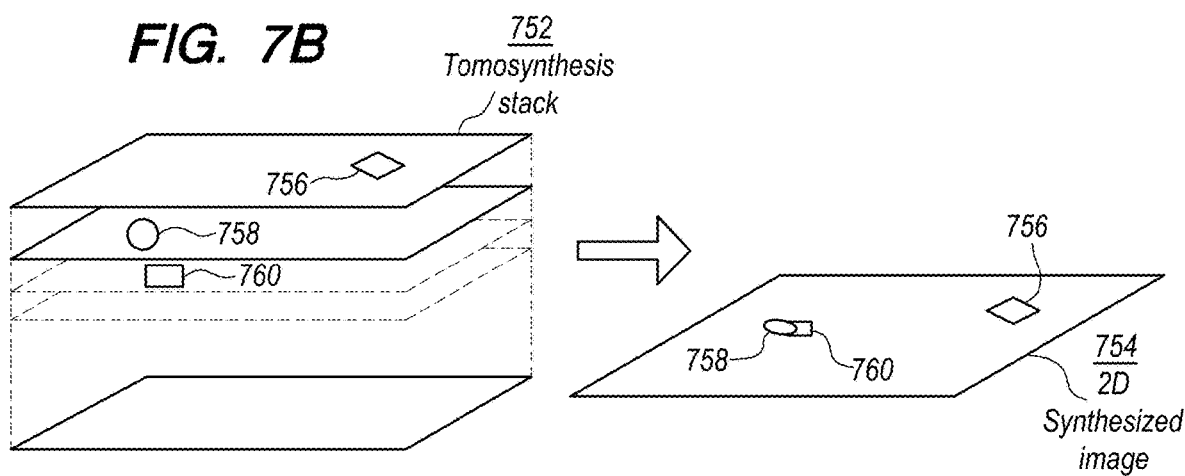

This approach to combining various object types in parallel is illustrated in FIG. 7B. In particular, the tomosynthesis stack 752 depict the same objects as FIG. 6B (e.g., objects 756, 758 and 760) at various image slices. As illustrated, objects 758 and 760 somewhat overlap in the z direction, which means that they are likely to compete for representation and/or overlap in the 2D synthesized image 754. Here, because the multiple target object recognition/enhancement modules are run in parallel, rather than one object type overriding another object type, as was the case in FIG. 6B, both the square-object 760 and the circular object 758 are fused together in the 2D synthesized image 754. Thus, this approach does not assume an innate priority/hierarchy between objects and all objects may be fused together appropriately in the 2D synthesized image 754.

Figure 8A:
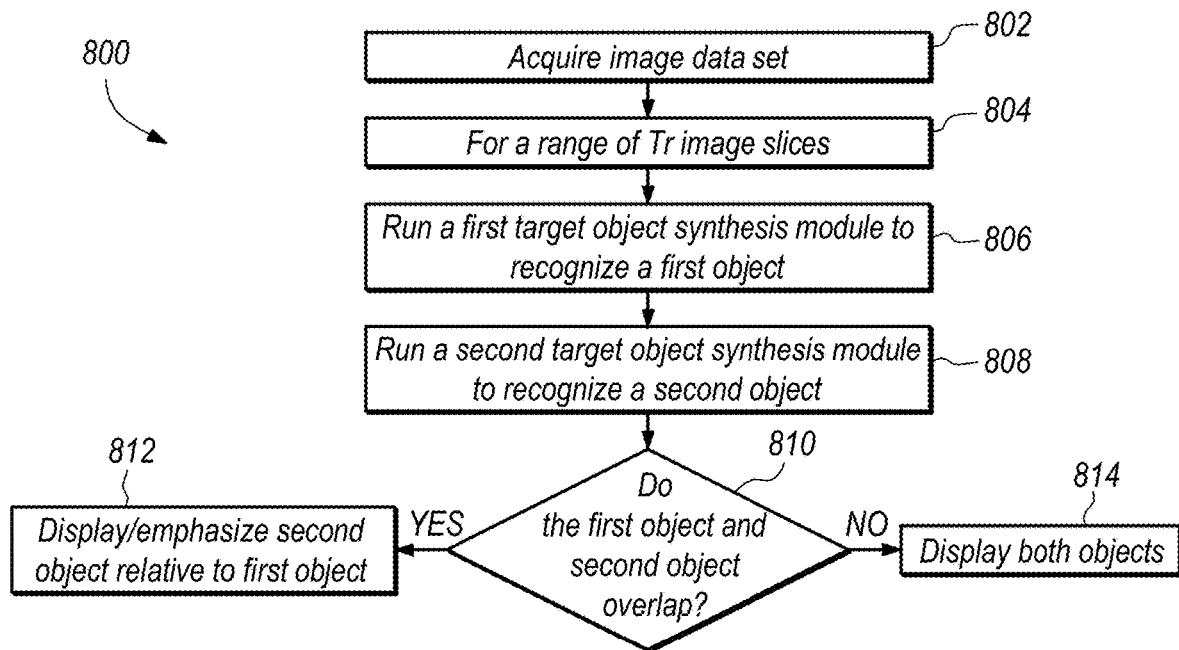
FIGS. 8A and 8B illustrate two example flow diagrams of generating 2D synthesized images using the sequential combination and parallel combination techniques respectively.

FIG. 8A depicts a flow diagram 800 that illustrates exemplary steps that may be performed in an image merge process carried out in accordance with the sequential combination approach outlined above in conjunction with FIGS. 6A and 6B. At step 802, an image data set is acquired. The image data set may be acquired by a tomosynthesis acquisition system, a combination tomosynthesis/mammography system, or by retrieving pre-existing image data from a storage device, whether locally or remotely located relative to an image display device, e.g., through a communication network. At steps 804 and 806, for a range of 2D images (e.g., Tr stack), a first target object recognition/enhancement module is run in order to recognize a first object associated with the first target object recognition/enhancement module. Any recognized objects may be stored in a storage module associated with the first target object recognition/enhancement module. At step 808, a second target object recognition/enhancement module is run in order to recognize a second object associated with the second target object recognition/enhancement module. At step 810, it may be determined whether the first recognize object and the second recognized object overlap each other in the z direction. If it is determined that the two objects overlap, only the second object may be displayed (or otherwise emphasized over the first object) on the 2D synthesized image at step 812. If, on the other hand, it is determined that the two objects do not overlap, both objects are displayed on the 2D synthesized image at step 814.

Figure 8B:
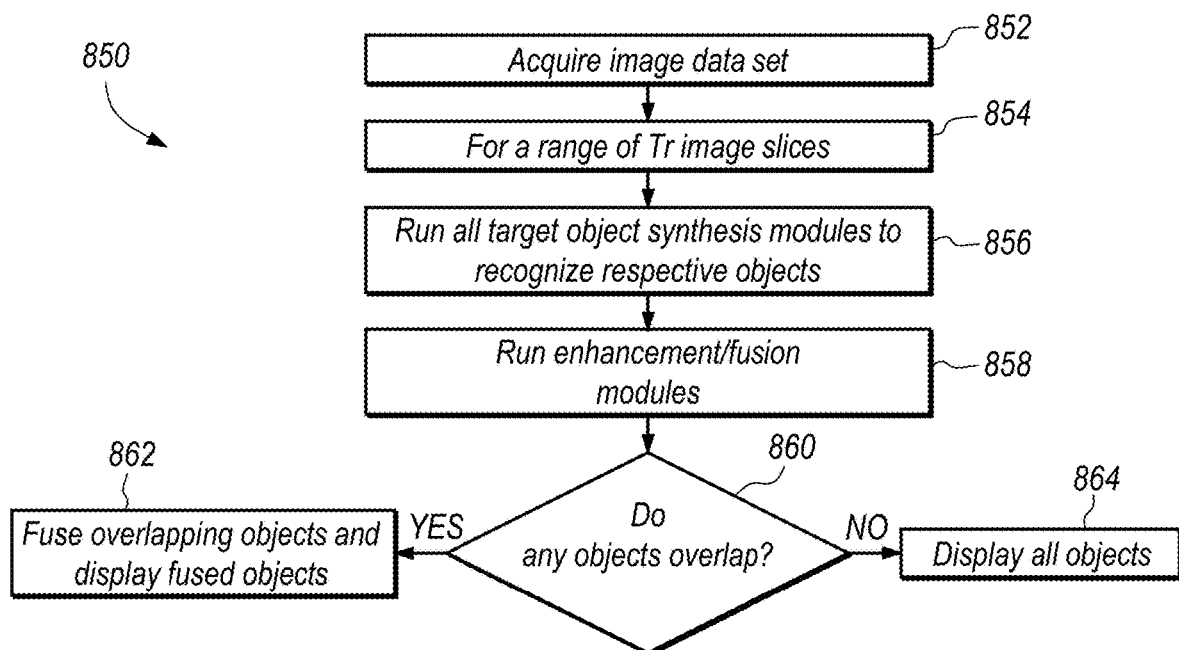

FIG. 8B depicts a flow diagram 850 that illustrates exemplary steps that may be performed in an image synthesis process carried out in accordance with the parallel combination approach outlined above in conjunction with FIGS. 7A and 7B. At step 852, an image data set is acquired. The image data set may be acquired by a tomosynthesis acquisition system, a combination tomosynthesis/mammography system, or by retrieving pre-existing image data from a storage device, whether locally or remotely located relative to an image display device. At steps 854 and 856, for a range of 2D images (e.g., Tr stack), all the programmed target object recognition/enhancement modules are run to recognize respective objects in the Tr image stack. At step 858, one or more enhancement modules may also be run to determine whether a fusion process needs to occur. At step 860, it may be determined whether any recognized objects overlap in the z direction. If it is determined that any two (or more) objects overlap, the overlapping objects may be fused together, at step 862. If, on the other hand, it is determined that no objects overlap, all the objects are displayed as is on the 2D synthesized image at step 814.

Having described how a 3D stack of image slices is generated and processed by a 2D synthesizer comprising target object recognition/enhancement modules in order to ensure that a synthesized 2D image displayed to a reviewer or end-user includes the most clinically relevant information, embodiments related to generating clearer, reduced shadow or shadow-free 2D synthesized images are described with reference to FIGS. 9-24. Embodiments described with reference to FIGS. 9-24 eliminate or reduce high density elements such as image portions depicting metal objects and/or shadows generated by imaging of same within 2D acquired or projection images and/or sets or stacks of 3D slices reconstructed based on 2D projection images. With embodiments, high density elements such as shadows are eliminated or reduced resulting in clearer 2D synthesized image that more accurately depicts breast tissue being analyzed and allows for more accurate and efficient radiologist examination since clinically relevant information is not blocked or obscured by shadows within the 2D synthesized image.

Figure 9:
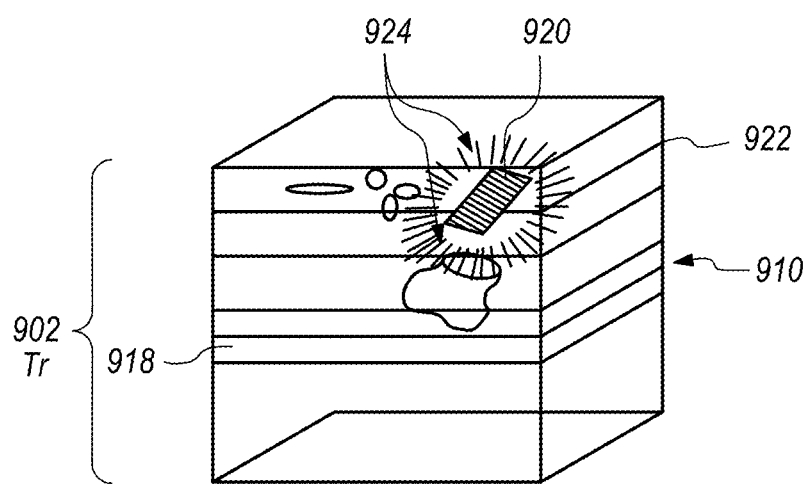
FIG. 9 depicts a 3D stack of image slices and how a high density element such as shadows generated by imaging metallic objects in breast tissue can obscure breast tissue and clinically important information.

Referring to FIG. 9, and referring again to FIGS. 1-2, reconstructed images Tr form a 3D tomosynthesis stack 902 of image slices 918. As a non-limiting example, a 3D tomosynthesis stack 902 may include about 30 to about 120 image slices Tr (e.g., ~60 image slides Tr) derived from or constructed based on about 15 or more 2D projection images Tp acquired by an x-ray image acquisition component 101 such as an x-ray source and detector collectively rotate around the patient or breast being analyzed. FIG. 9 depicts a 3D tomosynthesis stack 902 including image slices 918, e.g., similar to the stack 202 illustrated in FIG. 2. FIG. 9 further illustrates a high density element 920 in the breast tissue 910 and extending across multiple image slices 918. FIG. 9 illustrates the high density element 920 extending across two slices 918, but it will be understood that the high density element may extend to various depths.

An example of a high density element 920 is a metallic biopsy marker or clip, which may be made of stainless steel or titanium or other radiopaque or dense material. Another example of a high density element 920 is an external skin marker. A high density element 920 may also be a biological or tissue component within the breast tissue 910 such as a calcification or other dense biological or tissue structure that obscures other clinically relevant information or objects of interest in the breast tissue 910. A high density element 920 is also defined to include image artifacts generated thereby including shadows 922 generated by imaging or radiating a high density element 900 during breast imaging. Thus, a "high density element" may be a "foreign" or "external" object that is inserted into breast tissue 910 or attached to an outer breast surface 910 or be a naturally occurring material or component of breast tissue 910 having sufficient density to obscure other breast tissue that is clinically relevant information of breast tissue 910. For ease of explanation and not limitation, reference is made to a high density element 920, and a specific example of a metallic biopsy marker and a shadow 922 generated by imaging the metallic biopsy marker 920, but it will be understood that embodiments are not so limited.

The high density element 920 is illustrated as extending across multiple image slices 918. As generally illustrated in FIG. 9, the high density element 920 is denser than breast tissue 910 such that when imaged, a shadow 922 is generated, and the shadow 922 (as well as the metallic biopsy marker 920) obscures underlying and/or adjacent breast tissue 910 and clinically relevant information concerning same.

In the example generally illustrated in FIG. 9, the shadow 922 generated by imaging the metallic biopsy marker 920 is a "complete, "circumferential" or "global" shadow since the shadow 922 surrounds the metallic biopsy marker 920. Shadows may be caused from various aspects of image acquisition. For example, the type of shadow 922 generally depicted in FIG. 9 may result from one or more of the limited angle of tomosynthesis acquisition and reconstruction, also known as a reconstruction artifact, and image processing and enhancement, also known as an enhancement artifact. The illustrative shadow 922 depicted in FIG. 9 overlaps or obscures 924 objects of interest or clinically relevant information of breast tissue 910 such as lesions and spiculations. The depth and dimensions of shadows 922 depicted in the 3D tomosynthesis stack 902 (or in 2D projection images Tp) resulting from imaging of the high density element 920 may vary based on one imaging and/or material attributes including the angles of the x-ray source utilized and number of projection images Tp acquired, the metallic biopsy marker 920 material, and the size, shape and orientation of the metallic biopsy marker 920 being imaged. Thus, FIG. 9 is provided for purposes of general illustration, not limitation, to illustrate that a high density element in the form of a metallic biopsy marker 920 and/or shadow 922 depicted in one or more images may obscure clinically relevant information. Moreover, FIG. 9 illustrates a single high density element 920 in a 3D tomosynthesis stack 902, but there may be multiple high density elements 920, each of which may generate their own shadow 922, and which may be distinct and independent of each other or overlap with other shadows 922. Thus, multiple markers 920 and shadows 922 can further complicate generation and review of synthesized images since they may obscure relevant information from at multiple viewpoints.

Figure 10:
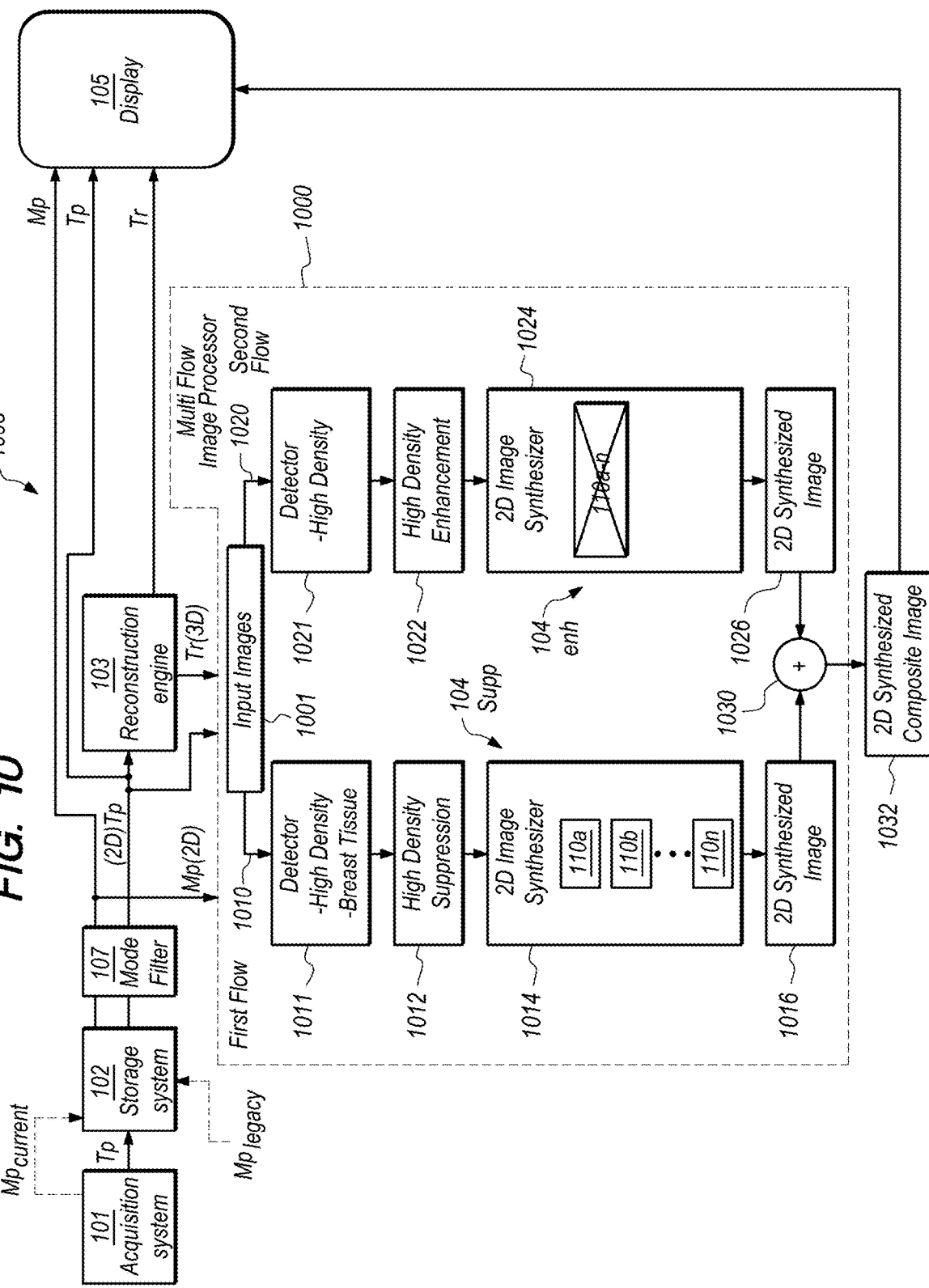
FIG. 10 is a block diagram illustrating the flow of data through an exemplary breast image acquisition and processing system in accordance with embodiments of the disclosed inventions involving selective suppression and enhancement of high density elements in breast images.

Referring to FIG. 10, embodiments of inventions provide breast image acquisition and processing systems 100s and multi-flow image processing methods 1000 that address complications with imaging high density elements 920 within breast images as discussed above with reference to FIG. 9 and provide for clearer and more accurate images that have reduced or are free of shadows for more accurate and efficient radiologist review. FIG. 10 illustrates a breast image generation and display system 100s ("s" referring to a breast image generation and display system that "suppresses" high density elements) constructed according to one embodiment and configured to execute a multi-flow or differential image processing method 1000 for selective high density element suppression and high density enhancement in breast images. Details of various system 100s components and interoperability thereof such as an acquisition system 101, storage system 102, reconstruction engine 103, a 2D image synthesizer 104 and a display 105 are discussed above with reference to FIGS. 1-8B and not repeated. Different images generated or processed thereby including acquired images, reconstructed images, synthesized images, Tp images (a 2D image acquired at respective tomosynthesis angles), Tr images (type (or subset) of a reconstructed image that is reconstructed from tomosynthesis projection images Tp) and Ms images (type (or subset) of a synthesized image, in particular, a synthesized 2D projection image that simulates mammography images) are also described above with reference to FIGS. 1-8B. For ease of explanation, embodiments of inventions are described with reference to 2D acquired images such as 2D projection images (e.g., Tp), reconstructed images (e.g., Tr) or a 3D stack 902 of image slices 918 and 2D synthesized images.

In the illustrated embodiment, the breast image generation and display system 100s includes a multi-flow image processor 1000 that is in communication with the reconstruction engine 103 and display 105. The image processor 1000 receives input images or digital image data 1001 of one or more types of images. The input image data 1001 (generally, input data 1001) may be for images of different dimensional formats such as 2D projection images and/or a 3D tomosynthesis stack 902 of image Tp slices 218. The input data 1001 is processed according to a first image processing flow or method 1010, and the same input data 1001 is processed with a second image processing flow or method 1020 different from the first processing flow or method 1010. The resulting 2D synthesized image is based at least in part upon high density element suppression and based at least in part upon high density element enhancement, and an image fusion or merge element 1030 combines the 2D synthesized images generated by respective image processing flows or methods 1010 and 1020 to generate a new 2D composite image 1032, which is communicated to display 105.

Thus, with the breast image generation and display system 100s, the same input data 1001 is processed in different ways according to different image processing flows to generate different 2D synthesized images, which are merged to generate a single 2D synthesized composite image 1034.

In the illustrated embodiment, the multi-flow image processor 1000 processes the same input data 1001 in different ways, which may be done by parallel and simultaneous image processing flows. In one embodiment, the input data 1001 is data of 2D projection images (Tp). In another embodiment, the input data 1001 is data of 3D images of a stack 902 of image slices 908. Different image processing methods executed based on the type of input data received are described in further detail below.

The input data 1001 received by the image processor is first processed in different ways, beginning with one or more image detectors 1011, 1021. Two image detectors 1011, 1021 are illustrated as the beginning of respective first and second image processing flows 1010, 1020. Image detector 1011 identifies and differentiates high density elements 920 and other elements such as breast tissue/background 910. Image detector 1021 identifies high density elements 920.

Image detectors 1011, 1021 may operate to distinguish a high density element 920 from breast tissue 910 or other image portions based on pre-determined filters or criteria involving, for example, one or more of image contrast, brightness, and radiopacity attributes. For example, high density element 920 may be associated with high contrast and brightness attributes compared to breast tissue or background 910 and thus be identified as a high density element. Detection criteria may involve a group of pixels or adjacent pixels having common characteristics, e.g., contrast or brightness within a certain range such that the group is identified as being a high density element. Image detectors may also distinguish a high density element 920 from best tissue based on shape, orientation and/or location data. For example, the image processor 1000 may be provide with specifications of known metallic biopsy markers. This data may be used in conjunction with image or pixel data such that image portions having similar properties also form a shape similar to a known shape of a biopsy marker, those pixels are identified as depicting a high density element 920. As another example, another factor that can be utilized to differentiate a high density element 920 is that skin markers are typically attached to an outer surface of the breast rather than being inserted into breast tissue. Thus, pixels having similar properties and being located at an outer surface indicative of an external skin marker are identified as a high density element 920. Location data can also be a factor, e.g., if a certain marker is inserted into a particular breast tissue region. Accordingly, it will be understood that image portions corresponding to high density elements and image portions corresponding to breast tissue or background 910 can be differentiated or detected in various ways using various filters, criteria and/or more sophisticated algorithms such as feature-based machine learning algorithms, or deep convolutional neural network algorithm.

Image detector 1011 is in communication with a high density element suppression module 1012, and image detector 1012 is in communication with a high density enhancement module 1024 such that respective detection results are provided to respective suppression and enhancement modules 1012, 1022. Respective outputs of respective high density element suppression and enhancement modules 1012, 1022 are provided as inputs to respective 2D image synthesizers 1014, 1024.

According to one embodiment, 2D image synthesizer 1014 used in the first image processing flow 1010 and that executes on high density element suppressed image portions operates in the same manner as 2D image synthesizer 104 that executes object enhancement and recognition modules 110a-n as discussed above with reference to FIGS. 1-8B, except that 2D image synthesizer 1014 receives high density suppressed image data. The 2D image synthesizer of the first image processing flow 1010 is thus referred to as 2D image synthesizer 104 supp ("supp" referring to high density element "suppressed"). Thus, 2D image synthesizer 1014 is configured to process high density element suppressed data while providing for breast tissue object enhancement and recognition via modules 110a-n.

In contrast, 2D image synthesizer 1024 does not involve high density element suppression or high density element suppressed data, and instead processes high density element enhanced image data while not enhancing breast tissue. In this manner, the focus of 2D image synthesizer 1024 is high density element 920 enhanced image data rather than breast tissue 910 enhancement such that 2D image synthesizer 1024 may also be referred to as 2D image synthesizer 104enh ("enh" referring to high density element "enhanced"). For this purpose, the 2D image synthesizer 1024 may not include object enhancement and recognition modules 110a-n or these object enhancement and recognition modules 110a-n may be deactivated. Thus, 2D image synthesizer 1024 is configured to process high density element enhanced data while breast tissue is not enhanced.

The 2D image synthesizer 1014/104supp outputs a 2D synthesized image 1016 that embodies high density element suppression and breast tissue enhancement data, and 2D image synthesizer 1024/104enh outputs a different 2D synthesized image 1026 that embodies high density element enhancement data. These different 2D synthesized images 1016, 1026 are provided as inputs to an image fusion or merging element 1030, which combines or merges the 2D synthesized images 1014, 1024 to generate a 2D composite synthesized image 1032 that incorporates elements of both of the 2D synthesized images 1014, 1024. Multi-flow image processing methods involving different types of input data 1001 and intermediate image and associated processing involving different dimensional formats and image or slice configurations are described in further detail with reference to FIGS. 11-24.

Figure 11:
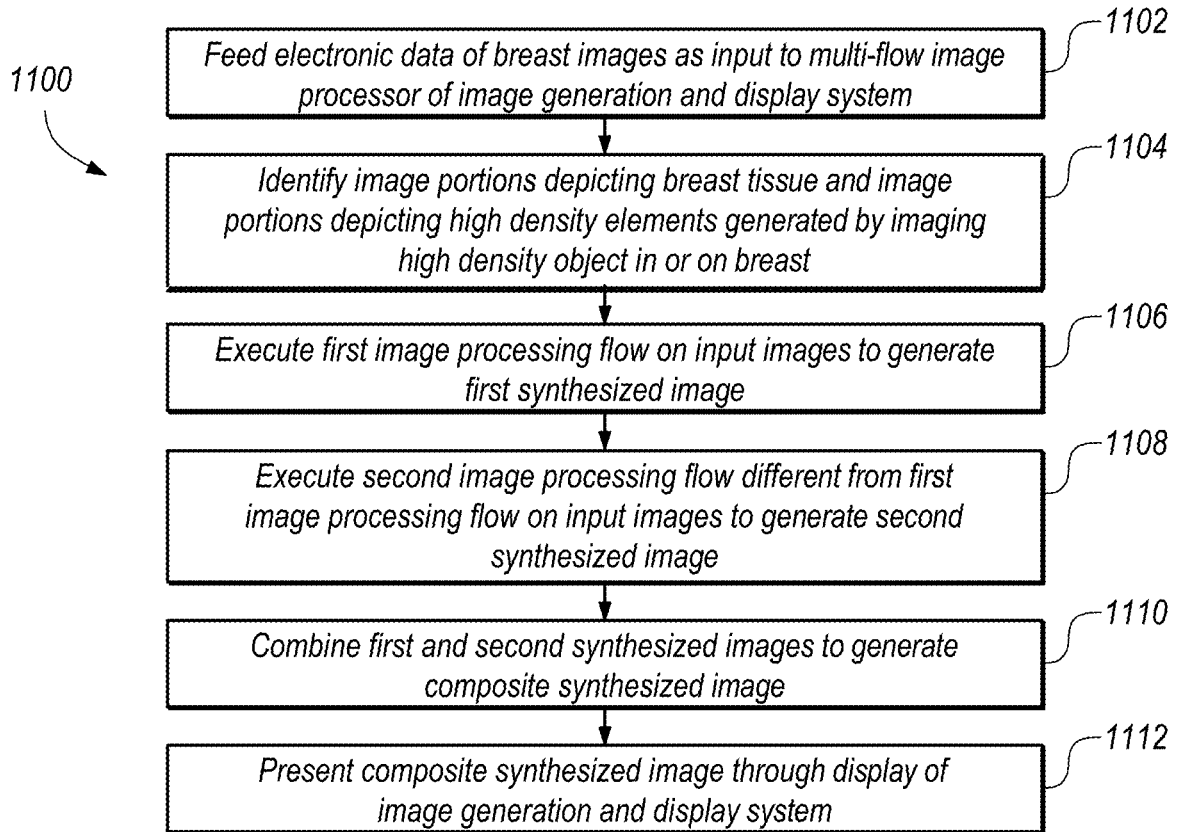
FIG. 11 illustrates a flow diagram of multi-flow or differential image processing executed to generate a composite 2D synthesized image according to one embodiment.

Referring to FIG. 11, in a multi-flow image processing method 1100 executed by breast image acquisition and processing system 100s according to one embodiment, at 1102, digital input data 1001 of one or more breast tissue images is fed as an input to a multi-flow or differential image processor 1000 of image generation and display system 100s such as a tomosynthesis system. At 1104, portions of images that depict breast tissue 910 and portions of images that depict high density elements 920 are identified or detected. A first image processing flow 1010 is executed on input data to generate first 2D synthesized image 1016.

Figure 12:
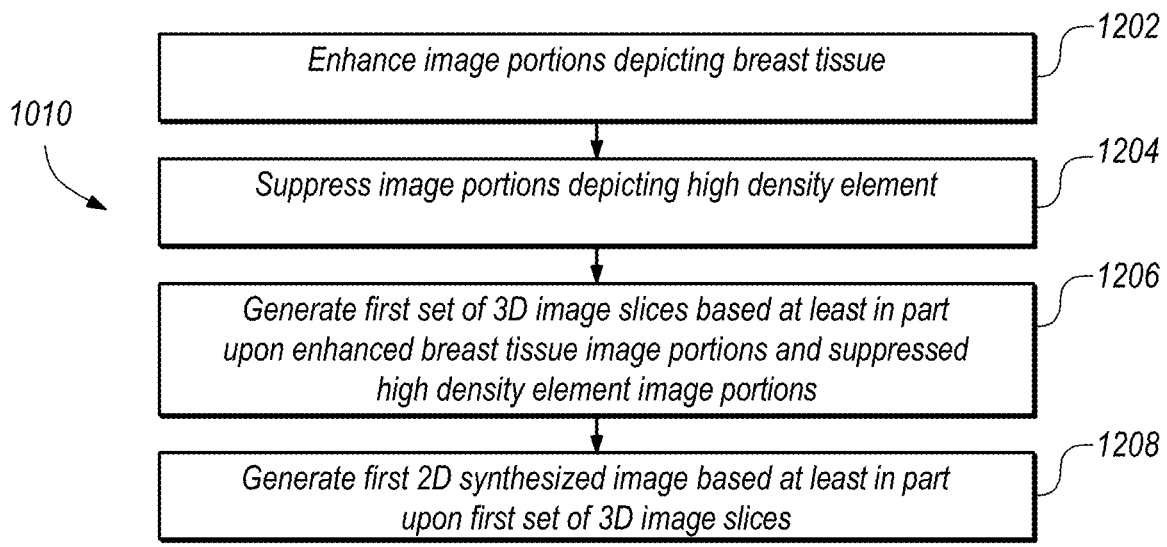
FIG. 12 illustrates a flow diagram of breast tissue enhancement and high density suppression of a first image processing flow executed on input images.

Referring to FIG. 12, the first image processing flow or method 1010, or metal suppression flow, includes enhancing image portions depicting breast tissue 910 at 1202, whereas image portions depicting a high density element 920 such as a metallic biopsy marker 920 and/or shadow 922 are suppressed, replaced or eliminated at 1204. At 1206, a first set or stack of 3D image slices (e.g., Tr slices) embodying enhanced breast tissue and suppressed high density element image portions is constructed, and at 1208, a first 2D synthesized image 1016 is generated based at least in part upon first stack of 3D image slices.

Figure 13:
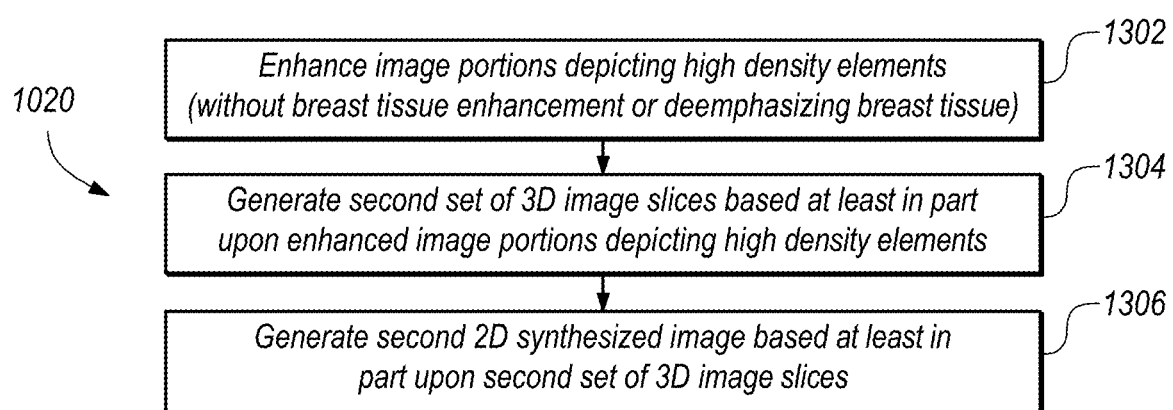
FIG. 13 illustrates a flow diagram of high density element enhancement of a second image processing flow executed on input images.

Referring to FIG. 13, the second image processing method 1020 is different from first image processing method 1010 and is executed on the same input data 1001. The second image processing method 1020 generates a different, second 2D synthesized image 1026. At 1302, image portions depicting high density elements 920 are emphasized (without breast tissue enhancement, or by deemphasizing breast tissue), at 1304, a second set of 3D image slices based at least in part upon enhanced image portions depicting high density elements is generated. At 1306, the second 2D synthesized image 1026 is generated based at least in part upon second set of 3D image slices.

Referring again to FIG. 11, at 1110, the first and second 2D synthesized images 1016, 1026 are combined or merged to generate composite synthesized image 1032, and at 1112, the composite synthesized image 1032 is presented through display 105 of image generation and display system 100s to a radiologist or end user.

Figure 14:
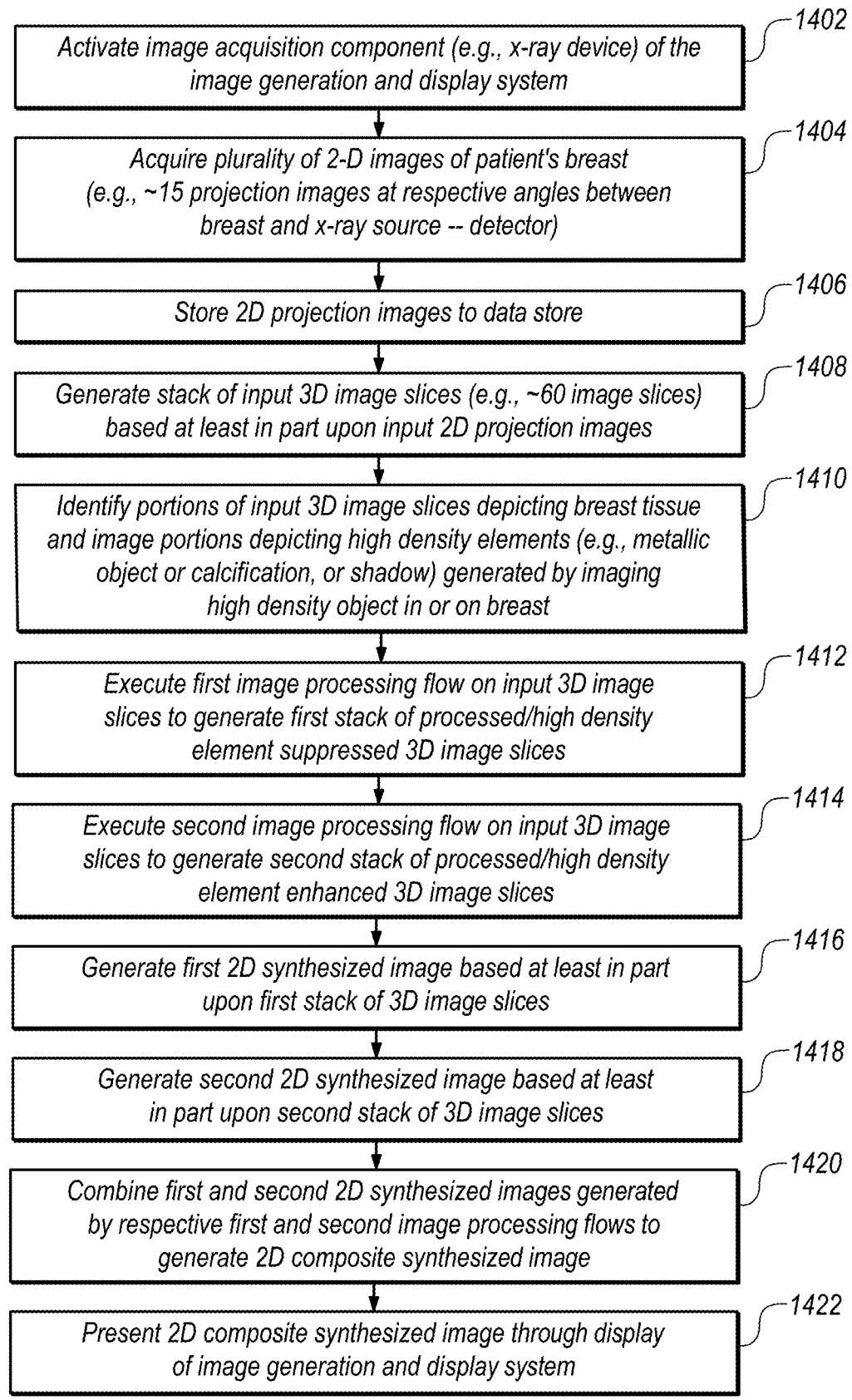
FIG. 14 illustrates a flow diagram of multi-flow or differential image processing that is executed directly on an input 3D stack of image slices.

Referring to FIG. 14 and with further reference to FIG. 15, one embodiment of a method 1400 for processing breast images using the system 100s configuration shown in FIG. 10 and as described with reference to FIGS. 11-13 is described. In method 1400, the multi-flow image processing method 1000 is executed on an input of a reconstructed 3D stack of image slices in which breast tissue 910 and high density elements 920 are both visible. Thus, in this embodiment, a stack of 3D image slices 1506 rather than 2D projection images 1502 are provided as an input 1501 to the image processor 1500 such that the multi-flow image processing method 1500 is not executed on 2D projection images 1502.

At 1402, image acquisition component 101 (e.g., x-ray device of digital tomosynthesis system)) is activated, and at 1404, a plurality of 2-D images 1502 of patient's breast is acquired. For example, in a tomosynthesis system, approximately 15 2D projection images Tp 1502 may be acquired at respective angles between the breast and the x-ray source—detector. It will be understood that 15 2D projection images is provided as an example of how many projection images may be acquired, and other numbers, greater than and less than 15, may also be utilized. At 1406, if needed, the acquired or projection images 1502 are stored by the acquisition component 101 to a data store 102 for subsequent retrieval, which may be from a data store 102 that is remote relative to the image processor 1000 and via a communication network.

At 1408, 2D projection image reconstruction 1504 is executed to generate a 3D stack 1508 of image slices Tr 1506 (e.g., ~60 image slices in the illustrative example). At 1410, the first detector 1511 of the first image processing flow 1510 identifies portions of input 3D image slices 1506 depicting breast tissue 910 and portions of image slices 1506 depicting high density elements 920 (e.g., metallic object or calcification, or shadow) generated by imaging high density element 920 in or on breast. A second detector 1521 identifies a high density element 920. For these purposes, the image processor 1500 may utilize one or more criteria or filters as described above to identify and differentiate breast tissue or background 910 and high density element image portions 920 in the 3D stack 1506.

Figure 15:
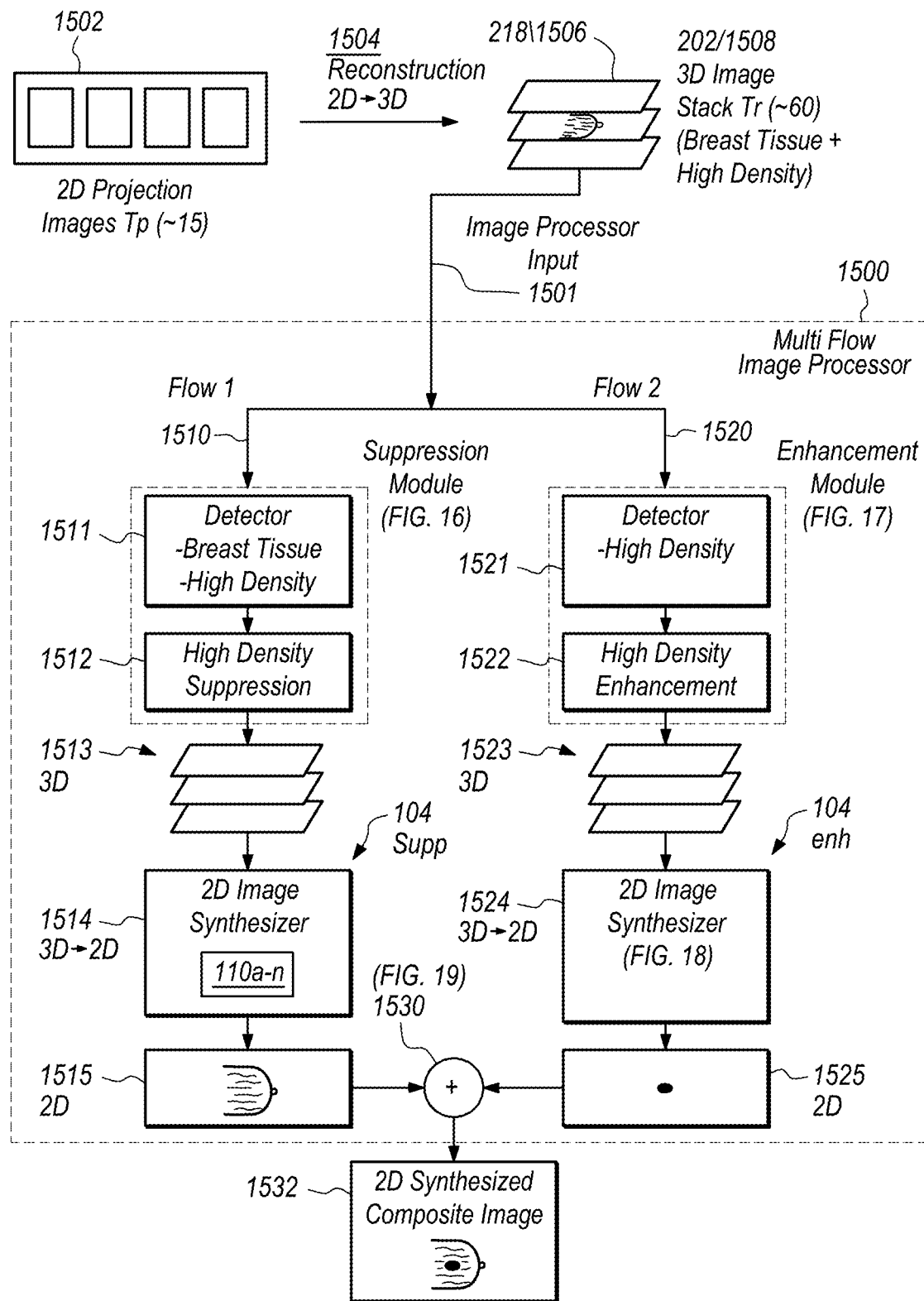
FIG. 15 illustrates an image-flow diagram illustrating an embodiment of multi-flow or differential image processing of FIG. 14 in which a multi-flow image processor receives inputs of 3D image slices.

Continuing with reference to FIGS. 14-15, at 1412, the first image processing flow 1510 involves high density element suppression 1512 of the input stack 1508, the result of which is generation of a first processed 3D stack 1513 in which a high density element 920 is suppressed or eliminated.

FIG. 16 illustrates in further detail one manner in which high density element suppression 1512 may be executed on the input 3D stack 1508 and also how an optional mask may be generated for subsequent use in generating a 2D synthesized composite image 1032. In the illustrated embodiment, the first image processing flow 1510 on the input 1501 of 3D image slices 1506 involves detection of portions of image slices 1506 depicting a high density element 920 such as a metallic biopsy marker at 1602, segmentation or pixel identification of the detected high density element portions 920 at 1604, and at 1606, a segmentation mask may be generated based on the segmentation results. The mask may be subsequently utilized when generating a 2D synthesized composite image 1032. At 1608, segmented portions are suppressed or eliminated from image slices of the 3D stack for high density element suppression. This may be done by interpolation or replacing segmented portions with other sampled portions of image slice background. High density element suppression results in the elimination of high density element 920 image portions from the 3D stack 1508 of image slices such that the high density element 920 would not be visually perceptible to a radiologist, or visually perceptible or to a lesser degree. Thus, the end result 1610 of the suppression process is a processed 3D stack 1610 of reconstruction image slices, or metal suppressed breast tissue slices, in which breast tissue image portions 910 are maintained while suppressing or eliminating image portions of high density elements 920, while also generating a separate "high density mask."

FIG. 17 illustrates in further detail one manner in which high density element enhancement 1522 within the input 3D stack 1508 may be executed and also how an optional segmentation or pixel mask may be generated for subsequent use in generating a 2D synthesized composite image 1032. In the illustrated embodiment, the second image processing flow 1520 on the input 3D image slices 1501 involves detecting portions of image slices depicting a high density element 920 such as a metallic biopsy marker at 1702, segmentation of the detected high density element portions at 1704, and at 1706, a segmentation mask may be generated and may be subsequently utilized when generating a 2D synthesized composite image 1032. Metal segmentation 1704 information may be recorded as a metal segmentation mask 1706, and masks from different slices can be combined into a single 2D metal mask, which is a side output from the metal synthesizer module 1524. As an example, in the case of using a binary mask, within this 2D metal mask image, the high density element regions are marked with 1 and the background or breast tissue regions are marked with 0. Different mask configurations or designs can also be utilized for these purposes by utilizing other or multiple labels rather than only binary "0" and "1" labels. At 1708, segmented portions are isolated and emphasized or enhanced in image slices of the 3D stack. High density element enhancement 1708 may be executed using, for example, maximum intensity projection or "MIP." The end result 1710 generated by the metal enhancement module is a stack 1523 of 3D reconstruction image slices in which breast tissue image portions 910 are not processed or not enhanced, and high density elements 920 are enhanced or emphasized.

Referring again to FIGS. 10 and 14-15, at 1414, the multi-flow image processor 1000 executes the first 2D image synthesizer 1514 that receives the processed or metal suppressed stack 1513 of 3D image slices as an input. The first 2D image synthesizer 1514 generates a 2D synthesized image 1515 based on the suppressed high density image portions of the metal suppressed 3D stack while enhancing or emphasizing breast tissue image portions by use of the target object recognition/enhancement modules (e.g., 110a, 110b . . . 110n), each configured for recognizing and enhancing a particular type of object. The first 2D image synthesizer 1514 may operate in the same manner as 2D image synthesizer 104 discussed above, except that the 2D image synthesizer receives image data resulting from high density element suppression 1512. As discussed above with reference to FIGS. 1-8B, target object recognition/enhancement modules 110a-n are configured to identify the respective object (if any is/are present) therein such that the resulting 2D synthesized images includes clinically-significant information.

Figure 18:
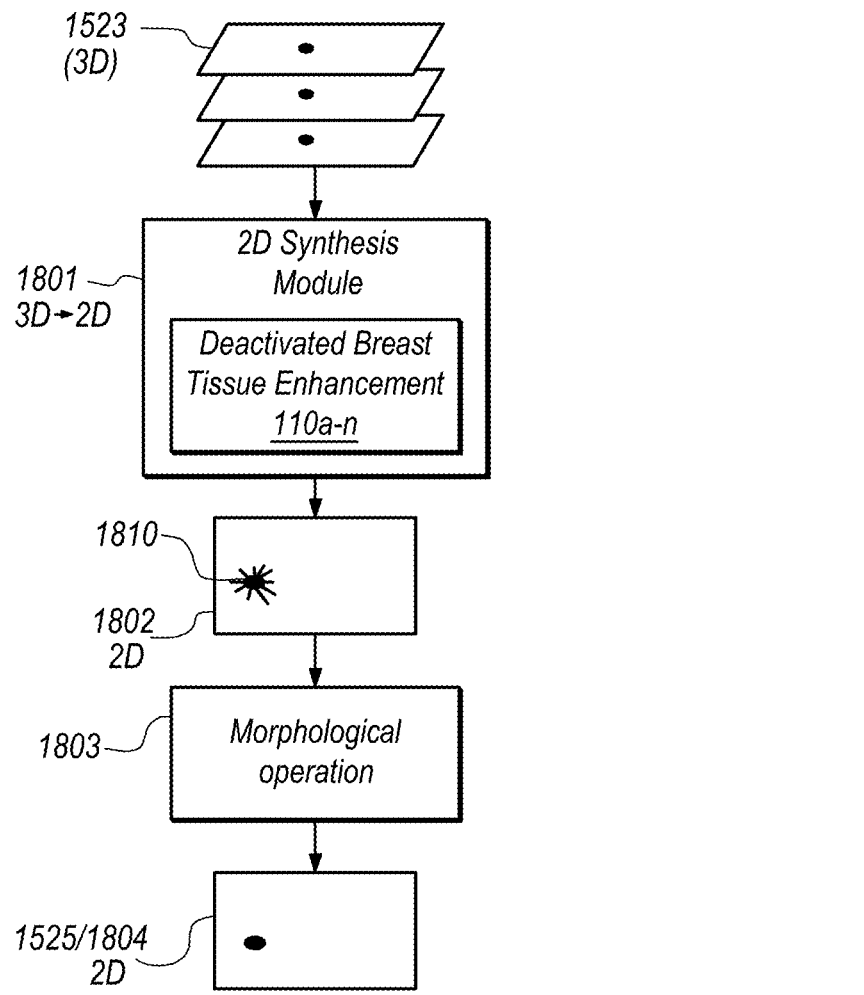
FIG. 18 illustrates an image-flow diagram of a 2D image synthesizer utilized in a second image processing flow in which high density elements are enhanced.

With continuing reference to FIGS. 14-15 and with further reference to FIG. 18, the multi-flow image processor 1000 executes the second 2D image synthesizer 1524/1801 that receives the processed or metal enhanced stack 1523 of 3D image slices as an input to generate a 2D synthesized image 1525/1802 based on the enhanced high density image portions of the metal enhanced 3D stack while other background or breast tissue portions are maintained or not enhanced, or even deemphasized, e.g., by reducing brightness thereof. For this purpose, the second 2D image synthesizer 1524 does not include, or deactivates, target object recognition/enhancement modules (e.g., 110a, 110b . . . 110n) such that these breast tissue analyses and enhancements are not performed and are not necessary in view of a high density element 920 structure. For example, a metallic biopsy marker may have a less complex geometric shape (e.g., a cylinder), or is typically less complex than breast tissue. For example, rather than employing more complicated target object recognition/enhancement 110a-n, the second image processing flow in which high density elements 920 are enhanced can deploy simply image processing algorithms such as mean-intensity projection or max-intensity projection as the base method to combine 3D stack of metal object slices into a single metal object 2D synthetic image 1810, which may be stored to a buffer. The result generated by the second 2D synthesizer 1524/1801 is generally illustrated by the high density object appearing as a "dot" in the 2D synthesized image 1525 1802 in FIG. 18.

FIG. 18 also illustrates the 2D synthetic image 1802 including various artifacts 1810 resulting from imperfections in metal detection and segmentation processes. Morphological operations 1803 (e.g. pixel dilation and/or erosion) can be executed on the 2D synthetic image 1802 to clean these artifacts 1810 by smoothing the high density object boundary to make the boundary in the resulting 2D image 1525/1804 more accurate and more visually appealing.

Referring again to FIGS. 14-15, having generated a first 2D synthesized image 1515 based at least in part upon first stack of 3D image slices and a second 2D synthesized image 1525 based at least in part upon second stack of 3D image slices, at 1420, these intermediate first and second 2D synthesized images 1515, 1525 generated by respective first and second image processing flows 1510, 1520 are merged or combined 1530 to generate a 2D final or composite synthesized image 1532, which is presented to a radiologist or end user via display 105 at 1422. According to one embodiment, image combination 1530 may involve selecting the best signals of 2D synthetic image data from each synthetic image buffer and ensuring that the transition between the breast tissue 910 and the high density element 920 is seamless. The 2D composite synthesized image 1532 is visually free of shadow artifacts 920 such that unwanted shadow artifacts do not obscure clinically important information while also including enhanced breast tissue or background and sharp delineations between breast tissue 910 and high density elements 920.

Figure 19:
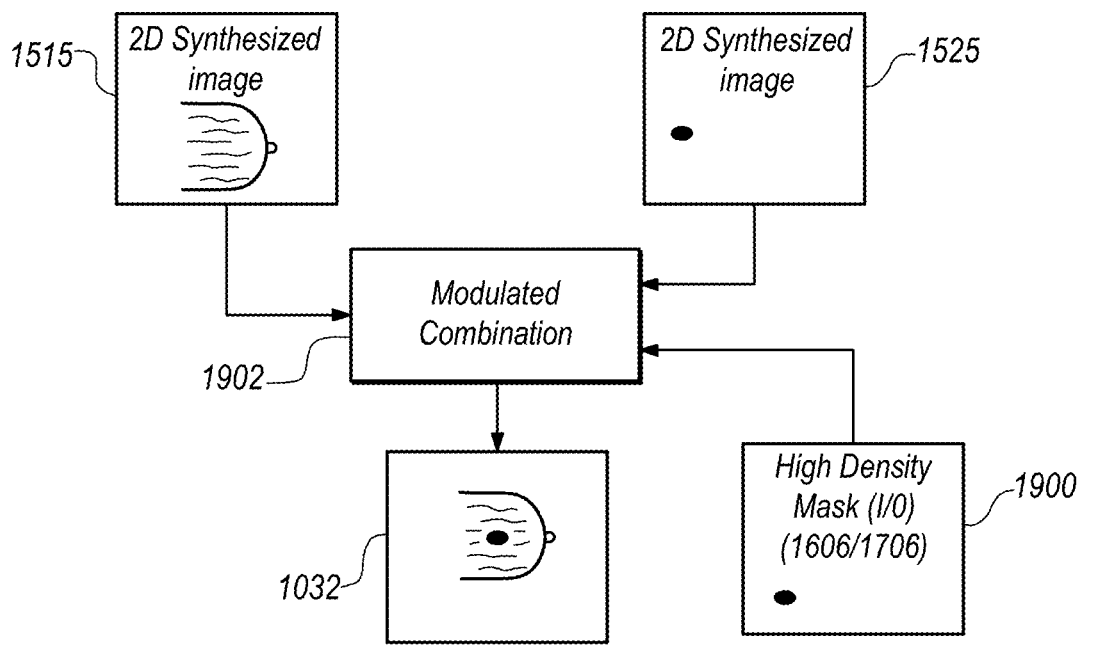
FIG. 19 illustrates an image-flow diagram of combining multiple 2D synthesized images to generate a 2D composite synthesized image.

Referring to FIG. 19, according to one embodiment of combining 1030 the first and second 2D synthesized images 1515, 1525, the 2D metal mask 1900 generated by segmentation as discussed above may be utilized for modulated combination 1902 or maximum intensity projection or "MIP" combination of the intermediate first and second 2D synthesized images 1515, 1525 to generate the 2D composite synthesized image 1532. This embodiment essentially extracts the signals or image portions from each 2D synthetic image 1515, 1525 buffer for seamless transition between breast tissue 910 and high density elements 920 such that the resulting 2D composite image 1032 is visually sharp, free of high density shadow elements while providing for optimal breast tissue background.

Figure 20A:
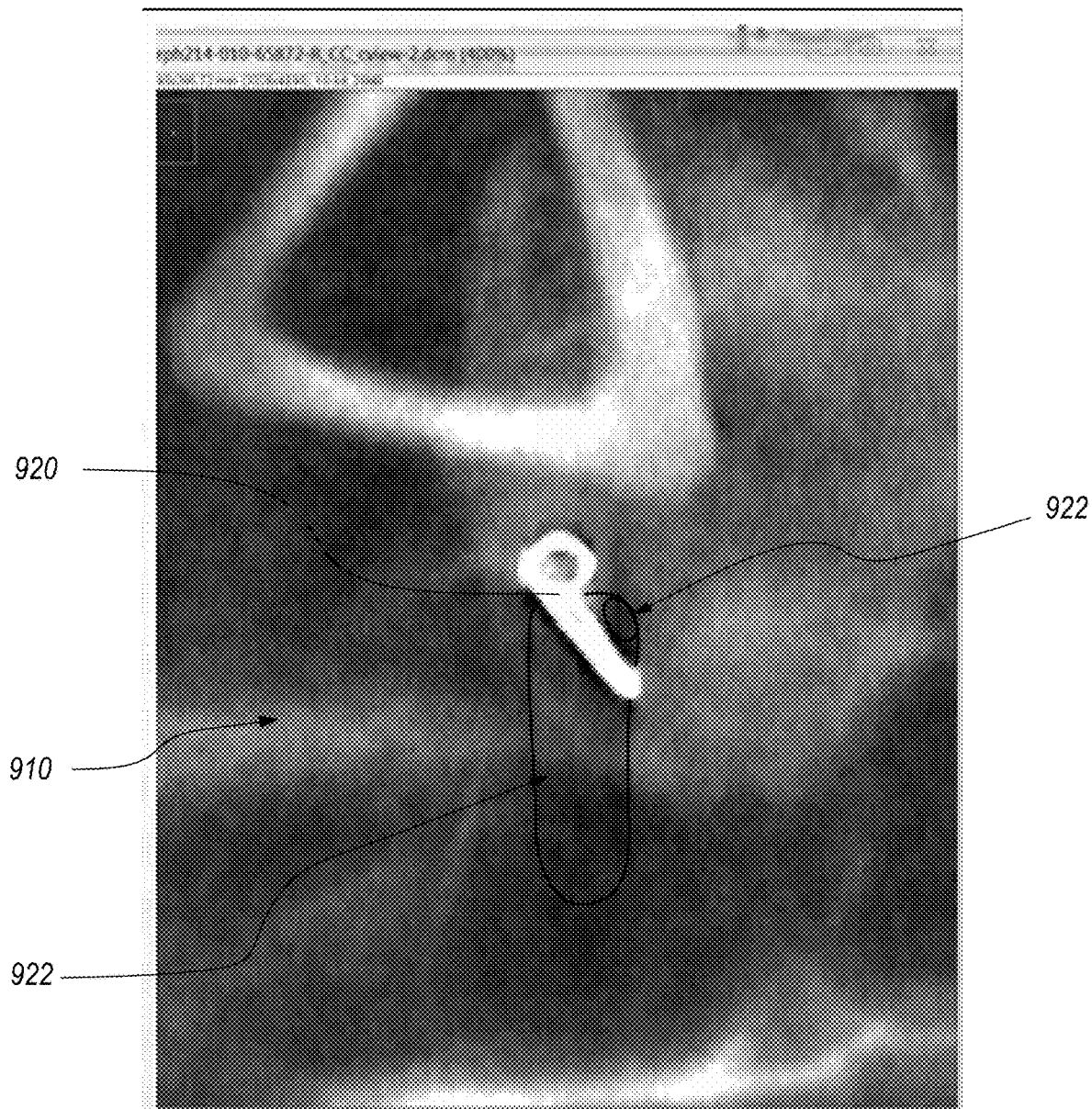
FIG. 20A depicts a 2D synthesized image showing how shadows generated by a metallic biopsy marker obscure breast tissue and clinically important information.
Figure 20B:
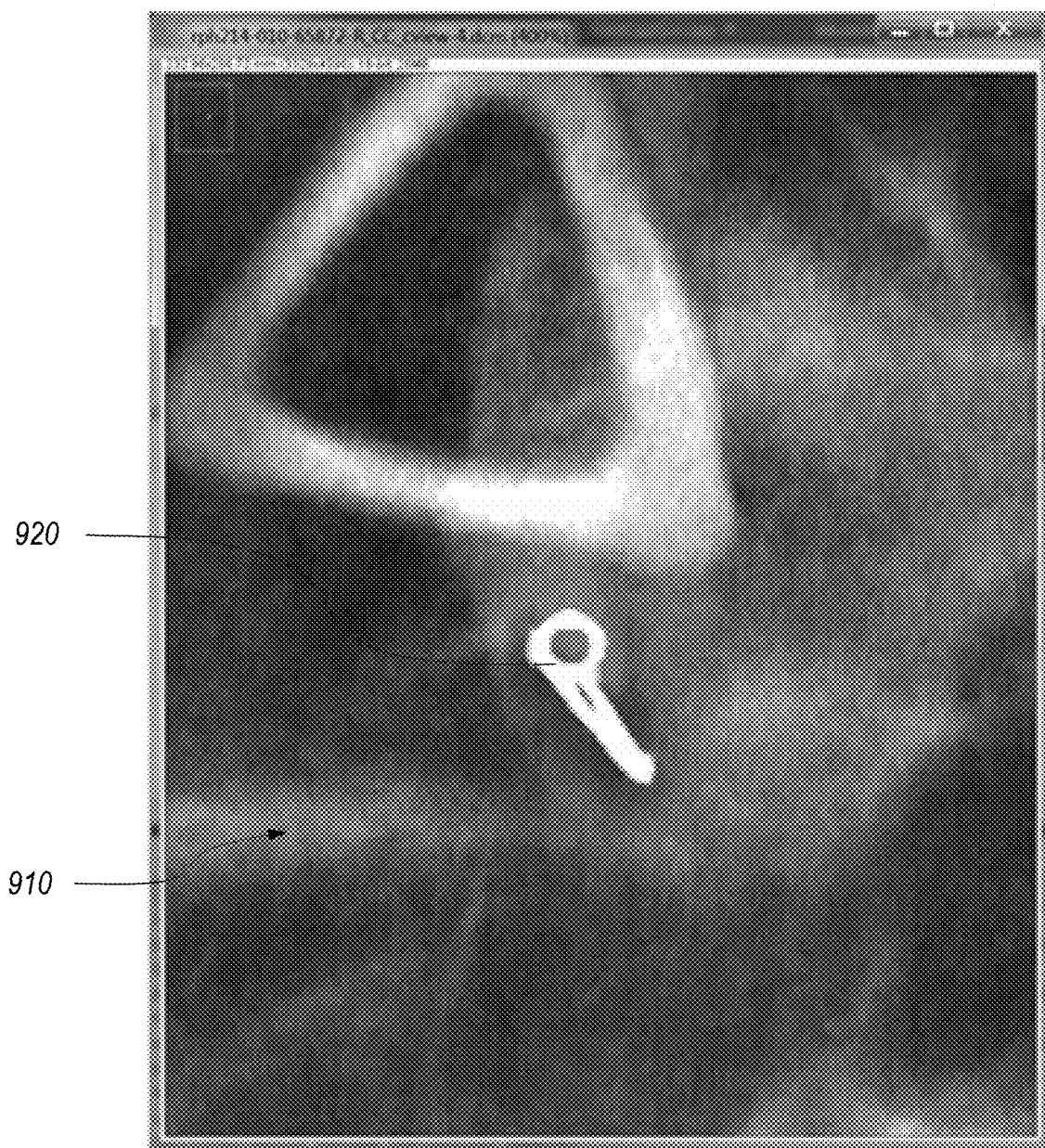
FIG. 20B depicts a 2D synthesized composite image generated according to embodiments and showing how shadows of FIG. 20A are suppressed or eliminated to provide for a clearer and unobstructed view of breast tissue and clinically important information.

FIGS. 20A-B illustrate an example of how multi-flow image processing embodiments can be executed to generate a 2D synthesized composite image 1032 that is visually sharp and clear with reduced or eliminated shadow 922 artifacts. FIG. 21B illustrates a 2D synthesized image 1032 that is constructed according to multi-flow image processing of embodiments that eliminates obscuring shadow artifacts 922 compared to FIG. 21A, which includes various shadow artifacts 922 around the metallic biopsy marker 920. The final result of a 2D synthesis composite image 1032 generated according to embodiments is sharp and shadow 922 free while breast tissue or background 910 is also enhanced.

Certain embodiments described above with reference to FIGS. 10-20B involve the multi-flow image processor 1500 receiving reconstructed or generated images or a 3D stack 1508 of image slices 1506 (e.g., ~60 reconstructed slices) as an input 1001 such that multi-flow image processing is executed on the same 3D stack 1508. The 3D stack 1508 is generated based on acquired 2D projection images 1502, which are not provided as an input 1001 to the image processor 1000 in these embodiments. Thus, the multi-flow image processing is not executed on the 2D projection images 1502 in these embodiments. In other words, the multi-flow image processing is executed directly on the 3D stack 1508 of image slices, but not the 2D projection images 1502 upon which the 3D stack 1508 of image slices is based, and the multi-flow image processing is executed after reconstruction 1504. Other embodiments may involve the image processor 1000 receiving inputs of different image types and dimensional formats.

For example, in other embodiments, the multi-flow image processor receives an input of 2D projection images such that the multi-flow image processing is executed directly on the 2D projection images rather than the 3D stack of image slices that is eventually generated after reconstruction. Different 3D stacks of image slices are provided as respective inputs to respective 2D image synthesizers after suppression and enhancement processing has been executed on 2D projection images. Thus, in certain embodiments, high density element suppression and enhancement occurs after reconstruction 1504 of a 3D stack 1508 of image slices 1506, whereas in other embodiments, high density element suppression and enhancement occur before reconstruction of a 3D stack of image slices. Alternative embodiments of multi-flow image processing involving execution of image processing embodiments using 2D projection images as an input to the image processor are described with reference to FIGS. 21-24. System components and their interoperability described above are not repeated.

Figure 22:
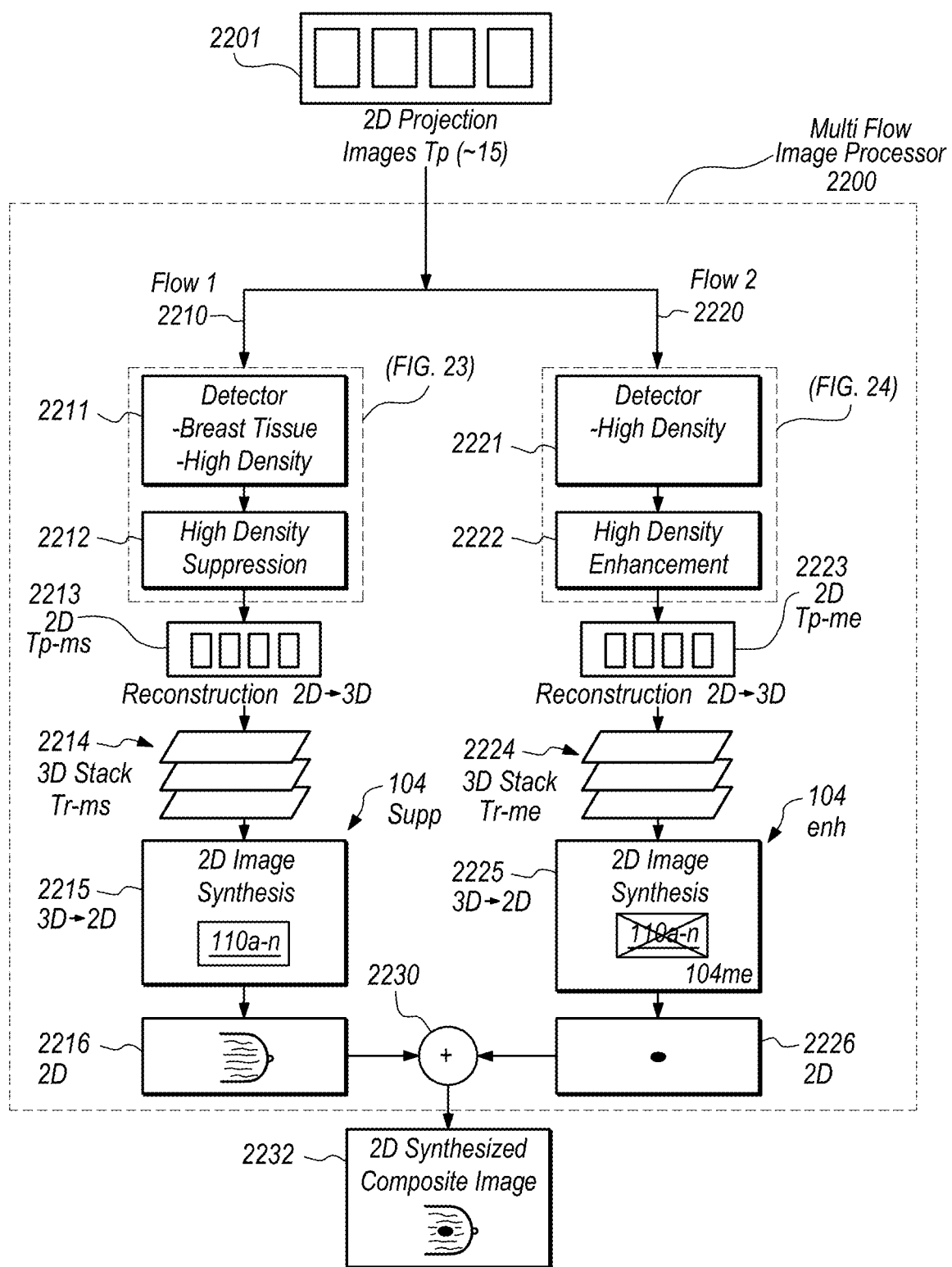
FIG. 22 illustrates an image-flow diagram illustrating an embodiment of multi-flow or differential image processing of FIG. 21 in which a multi-flow image processor receives inputs of 2D images.

Referring to FIGS. 21-22, in an image processing method 2100 according to another embodiment, at 2102, image acquisition component 101 (e.g., x-ray device) of the image generation and display system 100s is activated, and at 2104, a plurality of 2-D images of patient's breast 2201 (e.g., ~15 projection images at respective angles between breast and x-ray source—detector) is acquired. At 2106, 2D projection images 2201 are stored to a data store 102, and at 2108, digital image data of the 2-D projection images 2201 is received from the data store 102 and provided as an input to the multi-flow image processor 2200 of image generation and display system 100s. At 2210, a first detection module 2211 identifies portions of individual 2D projection images 2201 depicting breast tissue 910 and portions of individual 2D projection images 2201 depicting high density elements 920 (e.g., metallic biopsy marker or shadow) generated by imaging the metallic biopsy marker, and a second detection module 2221 identifies portions of individual 2D projection images 2201 depicting high density elements 920 (e.g., metallic object or shadow) generated by imaging high density object in or on breast.

At 2212, the first image processing method or flow 2210 including high density element suppression 2212 is executed on the input 2D projection images 2201 to generate processed/high density element suppressed 2D projection images 2213, and at 2214, the second image processing method or flow 2220 including high density element enhancement 2222 is executed on the input 2D projection images 2201 to generate processed/high density element enhanced 2D projection images 2223.

In certain embodiments, all of the input 2D projection images 2201 are suppressed in some way, whereas in other embodiments, only certain input 2D projection images 2201 are subjected to high density suppression 2212, e.g., only those determined to include at least a portion of a high density element 920. Thus, in certain embodiments, high density suppression 2212 and high density enhancement 2222 are both executed before any image reconstruction into a 3D stack of image slices. Further, in one embodiment, each input 2D projection image 2201 is processed such that the set of processed of 2D projection images 2213, 2223 is the same as the number of input 2D projection images 2201, but it will be understood that embodiments are not so limited. For example, the number of input 2D projection images 2201 that are subjected to high density element suppression 2212 and enhancement 2213 may be less than the number of input 2D projection images 2201 if only those input 2D projection images 2201 that are determined to include a high density element 920 are processed. Thus, for example, image acquisition may result in 15 input 2D projection images 2201, only eight of which contain at least a portion of a high density element 920, in which case only those eight input 2D projection images 2201 are processed for high density element suppression 2212 and enhancement 2222. The remaining seven input 2D projection images 2201 may be rejoined with the eight that were processed for a set of 15 projection images prior to reconstruction and generation of a 3D stack.

Accordingly, high density element suppression 2212 and enhancement 2222 may be executed before any 3D image reconstruction, on all of the 2D projection images 2201 of the input set, or on selected 2D projection images 2201 of the input set, e.g., those determined to contain high density elements by detector 2211, since a metallic object or shadow 920 generated thereby may not be present in certain images depending on the high density element size, location and orientation and position relative to a radiation source and detector used for imaging. Moreover, the number of processed 2D projection images 2213, 2223 following suppression 2212 and enhancement 2222 may be the same as the number of input 2D projection images 2201 even if only some of the input 2D projection images 2201 are processed since unprocessed input 2D projection images 2201 may be added to the processed set.

Continuing with reference to FIGS. 21-22, having generated the processed set of 2D projection images 2213, 2223, at 2216, a first stack 2214 of 3D image slices (e.g., ~60 image slices) is generated based at least in part upon the first set of processed 2D projection images 2213 (e.g., ~15 images) involving high density element suppression 2212, and at 2218, a second stack 2224 of 3D image slices is generated based at least in part upon the second set of processed 2D projection images 2223 involving high density element enhancement 2222.

Having constructed the first and second stacks of 3D images 2214, 2224, these stacks are then processed at 2120, 2122 by respective 2D image synthesizers 2215, 2225 to generate respective first and second 2D synthesized images 2216, 2226 based at least in part upon respective first and second stacks 2214, 2224. At 2124, morphological operations may be executed on the second 2D synthesized image 2226 as necessary to dilate or erode image edges of enhanced image portions depicting high density elements as necessary, and at 2226, the first and second 2D synthesized images 2216, 2226 are merged or combined 2230 to generate a 2D composite image at 2232, which is presented to the radiologist or end user via a display 105.

FIGS. 23-24 further illustrate how respective suppression 2212 and enhancement 2222 processing are executed, and are similar to the processing described with reference to FIGS. 15-17 above except that the detection, segmentation and suppression (FIG. 16) and suppression (FIG. 17) are based on inputs of individual input 2D projection images 1502 rather than on an input 3D stack of image slices, the resulting masks 2306, 2406 generated by segmentation is a mask for an individual image as shown in FIGS. 23-24 rather than for a stack of 3D image slices as shown in FIGS. 15-17, and the result or output of the suppression and enhancement processing is a suppressed or enhanced processed 2D projection image as shown in FIG. 22 rather than an output of a high density element suppressed 3D stack.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), without departing from the scope of the disclosed inventions, which is to be defined only by the following claims and their equivalents. The specification and drawings are, accordingly, to be regarded in an illustrative rather than restrictive sense.

What is claimed is:

1. A system comprising:
an x-ray image acquisition system having an x-ray source and an x-ray detector, the x-ray image acquisition system configured to generate a plurality of images of a patient's breast having image data;
a display coupled in communication to the x-ray image acquisition system;
an image processor; and
memory storing instructions that, when executed by the image processor, cause the system to perform a set of operations, the set of operations comprising:
feeding the image data as an input into the image processor;
identifying, by the image processor, image portions depicting breast tissue and image portions depicting a high density element generated by imaging the high density element together with breast tissue;
executing, by the image processor, a first image processing method comprising: enhancing identified image portions depicting breast tissue, suppressing identified image portions depicting the high density element, and generating, a first two-dimensional (2D) synthesized image based at least in part upon enhanced breast tissue image portions and suppressed high density element image portions;
executing, by the image processor, a second image processing method comprising: enhancing identified image portions depicting the high density element, and generating a second 2D synthesized image based at least in part upon enhanced high density element portions;
combining, by the image processor, the first 2D synthesized image generated by the first image processing method and the second 2D synthesized image generated by the second image processing method to generate a 2D composite synthesized image; and
presenting the 2D composite synthesized image through the display.

2. The system of claim 1, wherein the set of operations further comprises, before generating the first 2D synthesized image and generating the second 2D synthesized image:
generating, by the image processor, a first three-dimensional (3D) set of image slices based at least in part upon enhanced breast tissue images and suppressed high density element image portions, and generating a second 3D set of images slices based at least in part upon enhanced high density element image portions,
wherein the first 2D synthesized image is generated based at least in part upon the first 3D set of image slices, and the second 2D synthesized image is generated based at least in part upon the second 3D set of image slices.

3. The system of claim 1, wherein the set of operations further comprises acquiring, by the x-ray image acquisition system, a plurality of 2D projection images at respective angles of the breast, and wherein the first image processing method and the second image processing method are executed on image data of the 2D projection images.

4. The system of claim 1, wherein the set of operations further comprises:
activating the x-ray image acquisition system and acquiring a plurality of 2D projection images at respective angles of the breast; and
generating an input 3D stack of image slices based on the plurality of 2D projection images, the input 3D stack of image slices collectively depicting the breast, wherein the input to the image processor is the input 3D stack of image slices.

5. The system of claim 4, wherein within the set of operations, high density element suppression of the first image processing method and high density element enhancement of the second image processing method are not executed on the plurality of 2D projection images acquired by the x-ray image acquisition system.

6. The system of claim 5, wherein within the set of operations:
the first image processing method is executed on the input 3D stack of image slices to generate a first 3D stack of image slices, and the second image processing method is executed on the input 3D stack of image slices to generate a second 3D stack of image slices, and
the first 2D synthesized image is generated based at least in part upon the first 3D set of image slices, and the second 2D synthesized image is generated based at least in part upon the second 3D set of image slices.

7. The system of claim 6, wherein within the set of operations, the high density element is depicted as extending across multiple slices of the 3D input stack of image slices.

8. The system of claim 7, wherein within the set of operations, metal suppression of the first image processing method and metal enhancement of the second image processing method are not executed on the plurality of 2D projection images.

9. The system of claim 6, wherein within the set of operations, the first imaging processing method suppresses the identified image portions depicting the high density element such that the high density element is not visible in the first 3D stack of image slices.

10. The system of claim 1, wherein within the set of operations, identifying image portions depicting the high density element comprises identifying image portions depicting a metallic object in breast tissue, wherein image portions depicting the metallic object are suppressed by the first image processing method and enhanced by the second image processing method.

11. The system of claim 1, wherein within the set of operations, identifying image portions depicting the high density element comprises identifying image portions depicting a shadow cast by a metallic object as a result of imaging of the metallic object, wherein image portions depicting the shadow are suppressed by the first image processing method and enhanced by the second image processing method.

12. The system of claim 1, wherein within the set of operations, identifying image portions depicting the high density element comprises identifying image portions depicting a calcification in the breast tissue, wherein image portions depicting the calcification are suppressed by the first image processing method and enhanced by the second image processing method.

13. The system of claim 1, wherein within the set of operations, identifying image portions identifying the high density element comprises identifying image portions identifying a radiopaque object in breast tissue.

14. The system of claim 1, wherein within the set of operations, the first image processing method and the second image processing method are executed simultaneously in parallel.

15. The system of claim 1, wherein within the set of operations, the second image processing method enhances image portions depicting the high density element without enhancing image portions depicting breast tissue or lesions within the breast tissue.

16. The system of claim 1, wherein within the set of operations, image portions depicting the high density element are suppressed by replacing image portions depicting the high density element with background image data that is not enhanced.

17. The system of claim 1, wherein within the set of operations, the first 2D synthesized image is free of image portions depicting the high density element.

18. The system of claim 17, wherein within the set of operations, the first 2D synthesized image is free of image portions depicting the high density element and free of image portions depicting a shadow generated by imaging the high density element with the breast tissue.

19. The system of claim 1, wherein within the set of operations, the second 2D synthesized image is free of image portions depicting breast tissue.

20. The system of claim 1, wherein the x-ray image acquisition system is a tomosynthesis system.

* * * * *